United States Patent
Vogt et al.

(10) Patent No.: US 10,729,841 B2
(45) Date of Patent: Aug. 4, 2020

(54) FEMORAL HIP JOINT SPACER WITH IRRIGATION DEVICE

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 16/356,782

(22) Filed: Mar. 18, 2019

(65) Prior Publication Data

US 2019/0290833 A1    Sep. 26, 2019

(30) Foreign Application Priority Data

Mar. 21, 2018  (DE) .................. 10 2018 106 705

(51) Int. Cl.
*A61F 2/36* (2006.01)
*A61M 3/02* (2006.01)
(Continued)

(52) U.S. Cl.
CPC ............. *A61M 3/0283* (2013.01); *A61F 2/36* (2013.01); *A61F 2/4607* (2013.01);
(Continued)

(58) Field of Classification Search
CPC ........ A61F 2/36; A61F 2/4607; A61F 2/4684; A61M 3/0283
(Continued)

(56) References Cited

U.S. PATENT DOCUMENTS

| | | |
|---|---|---|
| 5,681,289 A | 10/1997 | Wilcox et al. |
| 6,245,111 B1 | 6/2001 | Shaffner |

(Continued)

FOREIGN PATENT DOCUMENTS

| | | |
|---|---|---|
| DE | 102015104704 | 10/2016 |
| EP | 1991170 | 11/2008 |

(Continued)

OTHER PUBLICATIONS

Australian Office Action dated Jun. 20, 2019 for Australian Patent Application No. 2019201731.
(Continued)

*Primary Examiner* — Bruce E Snow
(74) *Attorney, Agent, or Firm* — Stradley Ronon Stevens & Young, LLP

(57) ABSTRACT

A femoral hip joint spacer including a prosthesis body having a ball head with a sliding surface, a neck, a collar and a stem. A fastening area is arranged on the stem. The femoral hip joint spacer further has a first connector for feeding a medical irrigation liquid into the body, a second connector for draining the irrigation liquid from the body, and an irrigation liquid inlet opening. The first connector is connected in a liquid-conveying manner to the irrigation liquid inlet opening and an irrigation liquid outlet opening. The second connector is connected in a liquid-conveying manner to the irrigation liquid outlet opening, an irrigation liquid discharge opening and an irrigation liquid intake opening. The irrigation liquid discharge opening is connected inside the body to the irrigation liquid inlet opening and the irrigation liquid intake opening is connected inside the body to the irrigation liquid outlet opening.

20 Claims, 22 Drawing Sheets

(51) Int. Cl.
*A61F 2/46* (2006.01)
*A61M 39/10* (2006.01)
*A61M 39/24* (2006.01)
*A61F 2/30* (2006.01)

(52) U.S. Cl.
CPC .......... *A61F 2/4684* (2013.01); *A61M 39/10* (2013.01); *A61M 39/24* (2013.01); *A61F 2/4675* (2013.01); *A61F 2002/30405* (2013.01); *A61F 2002/30649* (2013.01); *A61F 2002/30672* (2013.01); *A61F 2002/30677* (2013.01); *A61F 2002/30805* (2013.01); *A61F 2002/3613* (2013.01); *A61F 2002/3627* (2013.01); *A61F 2002/4615* (2013.01); *A61F 2002/4631* (2013.01); *A61M 2205/04* (2013.01)

(58) Field of Classification Search
USPC ...................................................... 623/23.48
See application file for complete search history.

(56) References Cited

U.S. PATENT DOCUMENTS

| | | | | |
|---|---|---|---|---|
| 8,939,933 | B2* | 1/2015 | Santora | A61M 1/0084 604/131 |
| 2007/0179609 | A1* | 8/2007 | Goble | A61B 17/86 623/16.11 |
| 2007/0219471 | A1 | 9/2007 | Johnson et al. | |
| 2008/0058950 | A1 | 3/2008 | Leonard et al. | |
| 2010/0042213 | A1 | 2/2010 | Nebosky et al. | |
| 2010/0168688 | A1 | 7/2010 | Santora et al. | |
| 2010/0247401 | A1 | 9/2010 | Barthe et al. | |
| 2011/0015754 | A1 | 1/2011 | Leonard et al. | |
| 2013/0187310 | A1 | 7/2013 | Vogt et al. | |
| 2013/0211369 | A1 | 8/2013 | De Beaubien | |
| 2016/0332328 | A1 | 11/2016 | Wust et al. | |
| 2017/0354507 | A1 | 12/2017 | Foran | |
| 2018/0028320 | A1 | 2/2018 | Forsell | |

FOREIGN PATENT DOCUMENTS

| | | |
|---|---|---|
| EP | 2617393 | 7/2013 |
| WO | 2012030331 | 3/2012 |
| WO | 2017178951 | 10/2017 |

OTHER PUBLICATIONS

Canadian Office Action dated Apr. 24, 2020 for Canadian Patent Application No. 3035583.

\* cited by examiner

FEMORAL HIP JOINT SPACER WITH IRRIGATION DEVICE

RELATED APPLICATION

This application claims the benefit of priority to German Patent Application Number DE 10 2018 106 705.4, filed on Mar. 21, 2018, the contents of which are incorporated in this application by reference.

TECHNICAL FIELD

The invention relates to a femoral hip joint spacer for temporary replacement of at least one part of a hip joint, which is intended for the interim phase of two-stage septic revisions of hip joint endoprostheses. The hip joint spacer may be used in particular in two-stage septic revisions in which two or more microbial microorganisms are the cause of an infection in the hip joint endoprosthesis and the surrounding tissue.

BACKGROUND OF THE DISCLOSURE

Hip joint endoprostheses are implanted in large numbers worldwide. Unfortunately, in a small percentage of cases, hip joint endoprostheses are colonized by microbial microorganisms, particularly Gram-positive bacteria and also Gram-negative bacteria, and to a very small extent by yeasts and fungi. These microbial microorganisms, mainly typical skin microbes such as Staphylococcus aureus and Staphylococcus epidermidis, may enter a patient's body during a surgical operation (OP). It is also possible for microbial microorganisms to enter hip joint endoprostheses hematogenically. Where hip joint endoprostheses are colonized by microbial microorganisms, the surrounding bone and soft tissue also become infected and damaged by the microbial microorganisms.

The prior art primarily encompasses two treatment methods for infected hip joint endoprostheses, one-stage septic revision and two-stage septic revision. There are also a number of further treatment methods, such as for example the application of suction/irrigation drains.

In the case of one-stage revision, within one OP first of all the infected hip joint endoprosthesis is removed, next radical debridement is performed and then a revision hip joint endoprosthesis is implanted.

In two-stage septic revisions, in a first OP the infected hip joint endoprosthesis is initially removed, then debridement is performed and thereafter a hip joint spacer is implanted. The hip joint spacer consists of a stem, a collar, a neck and a ball head and replicates hip joint endoprostheses in shape and size. The hip joint spacer is anchored to the proximal femur with bone cement. The hip joint spacer remains for up to several weeks in the patient until the inflammation has subsided and the clinical inflammation markers have receded. The hip joint spacer is then removed in a second OP and a revision hip joint endoprosthesis implanted after fresh debridement.

US 2010/0042213 A1 discloses a hip joint prosthesis with a reservoir for liquid inside the implant. A hip spacer is known from WO 2017/178951 A1 which has recesses, wherein a substance for treating the bone may be introduced into the recesses. U.S. Pat. No. 6,245,111 B1 proposes a hip joint prosthesis, the surfaces of which are coated with an antibiotic. U.S. Pat. No. 5,681,289 B1 discloses a device for distributing a liquid active ingredient with the assistance of a bladder inside the device.

It is known to use spacers provided with antibiotics. Hip joint spacers may on the one hand be produced by the OP personnel during the OP itself from PMMA bone cement powder, antibiotics and monomer liquid, for example with a spacer shape, as described for example in patents DE 10 2015 104 704 B4 or EP 2 617 393 B1; on the other hand it is also conventional to use hip joint spacers prefabricated industrially from bone cement.

In spacers to date, antibiotics have been added to the cement powder before actual spacer production. Spacers are then cast using this antibiotically modified bone cement powder and subsequently harden by polymerization with the assistance of a monomer liquid added to the cement powder. The bone cement paste thus substantially encloses the antibiotics. Only the antibiotic particles situated in areas close to the surface are released under the action of bodily fluids, such as wound secretions. Active ingredient release is greatest at the start and then diminishes over the course of several days. Thereafter, only small quantities of the antibiotics continue to be released. The majority of the added antibiotics remains in the hardened bone cement of the spacers. In the case of spacers hitherto manufactured from bone cement, a subsequent change in the type and number of antibiotics used is not possible after spacer production or after implantation. It is moreover likewise impossible to adjust a defined concentration of antimicrobially active ingredients in the wound secretions or the bodily fluid surrounding the spacer.

In patent EP 1 991 170 B1 a hip joint spacer is described in which the ball head and the stem may be assembled by the user, wherein the ball head contains a first active ingredient and the stem is provided with a second active ingredient.

A further hip joint spacer is disclosed in US 2011/0015754 A1. In this spacer system, two cylindrical cavities are provided in the ball head which emerge with a narrow side at the ball surface. The two cavities are each closed with a liquid-permeable cap. Both cavities may be filled with antibiotic solutions. After implantation, the antibiotic solutions migrate through the liquid-permeable caps to the surface of the spacer.

In the case of two-stage septic revision, drains are also used during implantation of the hip joint spacers, these being intended to carry away wound secretions, blood and debris. The drains remain inside the patient for up to several days. The antibiotic active ingredients released by the spacer are taken up by the wound secretions and carried out via the drain. This means that a proportion of the antimicrobial active ingredients for protecting the spacer surface from microbial colonization are lost.

SUMMARY OF THE INVENTION

It was identified, for the purposes of the present invention, that it would be desirable for the spacer surface to be surrounded by an antimicrobial active ingredient solution, the active ingredient concentration of which can be precisely adjusted and the concentration of which would be maintained for several days irrespective of wound secretion flow. It would moreover be desirable to be able to vary the type and number of microbial active ingredients even after implantation of the hip joint spacer, so as to be able to respond to microbial microorganisms only detected later, for instance. At the same time, the patient needs to be able to move the hip joint, to prevent the tendons and muscles from shortening and the muscles from degenerating and thereby to reduce rehabilitation time.

An object of the present invention thus consists in overcoming the disadvantages of the prior art. In particular, an object of the invention consists in developing a temporary femoral hip joint spacer with which a medical irrigation liquid can be used in a targeted manner in the hip region. At the same time, the hip joint spacer is intended to allow hip joint mobility when in use in a patient.

An object of the invention is in this respect to develop an articulating hip joint spacer which is intended for the interim phase of two-stage septic hip joint endoprosthesis revisions and which has characteristics which are beneficial for this purpose. The hip joint spacer is intended to fill the space after removal of the hip joint endoprosthesis and subsequent debridement in such a way as to prevent ligament and muscle degeneration. The hip joint spacer is intended to enable the articulating spacer surface, the soft tissue surrounding the hip joint spacer and at least a proportion of the surrounding bone tissue to be irrigated continuously or indeed discontinuously with antiseptic or antibiotic irrigation liquids. The hip joint spacer is intended to be able to be connected to the bone tissue of the proximal femur with bone cement in such a way that exit of the irrigation liquid from the stem or in the region of the stem of the hip joint spacer and also uptake of the irrigation liquid into the hip joint spacer for drainage are not disturbed or interrupted. The nature of the hip joint spacer is furthermore intended as far as possible to be such that, after completion of irrigation with the irrigation liquid, the irrigation liquid feed line and the irrigation liquid drain line can be removed without impairing hip joint spacer articulation.

The objects of the invention are achieved by a femoral hip joint spacer for temporary replacement of part of a hip joint, the hip joint spacer having:

A) a prosthesis body, the prosthesis body having a ball head with a sliding surface, a neck, which is connected to the ball head, a collar, which is connected on a proximal side to the neck, and a stem, which is connected to a distal side of the collar, wherein at least one fastening area is arranged on the stem of the prosthesis body, B) the hip joint spacer further having a first tubular and liquid-conveying connector for feeding a medical irrigation liquid into the prosthesis body, C) a second tubular and liquid-conveying connector for draining the irrigation liquid from the prosthesis body, D) an irrigation liquid inlet opening in a surface of the prosthesis body, wherein the first connector is connected or connectable in a liquid-conveying manner to the irrigation liquid inlet opening, E) an irrigation liquid outlet opening in the surface of the prosthesis body, wherein the second connector is connected or connectable in a liquid-conveying manner to the irrigation liquid outlet opening, F) at least one irrigation liquid discharge opening and at least one irrigation liquid intake opening, which are arranged in the surface of the prosthesis body outside the at least one fastening area, wherein the at least one irrigation liquid discharge opening is connected inside the prosthesis body in a liquid-conveying manner to the irrigation liquid inlet opening and the at least one irrigation liquid intake opening is connected inside the prosthesis body in a liquid-conveying manner to the irrigation liquid outlet opening.

The irrigation liquid may theoretically also initially be introduced through the first connector and drained through the second connector and then introduced through the second connector and drained through the first connector. The hip joint spacer is then operated in alternating manner. It is preferred according to the invention, however, for the hip joint spacer to be operated or operable in just one flow direction of the irrigation liquid.

The first tubular liquid-conveying connector is preferably a hose with an adapter or another connection.

The second tubular liquid-conveying connector is preferably a hose with an adapter or another connection.

In the present patent application, the statements of direction ("proximal," "distal" and "lateral") and the statements relating to planes ("sagittal plane," "front plane" and "transverse plane") relating to the hip joint spacer are used in such a way as would be understood as a main anatomical direction or body plane when inserted into the patient. For instance, "proximal" means towards the center of the body and "distal" means remote from the center of the body.

Provision may preferably be made for the hip joint spacer to be suitable for the application of an antibiotic active ingredient which prevents or impairs polymerization or free-radical polymerization of PMMA. Provision may in particular be made for the hip joint spacer to be suitable for the application of rifampicin and metronidazole.

In hip joint spacers according to the invention, provision may be made for the at least one fastening area to be delimited or for the at least one fastening area to be delimited by a peripheral rib extending up out of the surface of the prosthesis body, such that the at least one fastening area is suitable for accommodating bone cement paste within the rib.

In this way, a delimited and thereby specific region may be used for fastening the prosthesis body. When the hip joint spacer is used correctly, this may prevent the first and second connectors and the irrigation liquid inlet opening and the irrigation liquid outlet opening from being covered with bone cement and their function thereby being impaired. It is in particular possible to prevent the hardened bone cement from preventing the first and second connectors from being pulled away or detached from the prosthesis body.

Provision may in this respect be made for at least one of the at least one fastening area to be regionally delimited by a part of the collar.

This provision ensures a particularly robust connection of the hip joint spacer with the femur. At the same time, however, space still remains for the at least one irrigation liquid discharge opening and for the at least one irrigation liquid intake opening outside the at least one fastening area, such that in this region irrigation with the irrigation liquid may take place without the openings becoming sealed with the bone cement paste for fixing the hip joint spacer to the femur.

According to one particularly preferred embodiment of the hip joint spacer according to the invention, provision may be made for at least one first irrigation liquid discharge opening and at least one first irrigation liquid intake opening to be arranged in the surface of the prosthesis body on the distal side of the collar or on the stem outside the at least one fastening area, and for at least one second irrigation liquid discharge opening and at least one second irrigation liquid intake opening to be arranged in the surface of the prosthesis body to the side of the collar or on the proximal side of the collar or on the neck or on the ball head, wherein the at least one first irrigation liquid discharge opening and the at least one second irrigation liquid discharge opening are connected inside the prosthesis body in a liquid-conveying manner to the irrigation liquid inlet opening and wherein the at least one first irrigation liquid intake opening and the at least one second irrigation liquid intake opening are connected inside the prosthesis body in a liquid-conveying manner to the irrigation liquid outlet opening.

In this way, two separate irrigation liquid circuits are produced, which run separately from one another on the distal and proximal sides of the hip joint spacer. The collar, which would impede the flow of irrigation liquid, does not then have to be flowed round in order to be able to irrigate both sides of the hip joint spacer effectively with the irrigation liquid.

Provision may in this respect be made for the at least one first irrigation liquid discharge opening and the at least one first irrigation liquid intake opening to be spaced from one another and for the at least one second irrigation liquid discharge opening and the at least one second irrigation liquid intake opening to be spaced from one another, wherein the distance amounts to at least 5 mm, preferably at least 20 mm and particularly preferably at least 30 mm.

In this way, it is ensured that the medical irrigation liquid circuit has to cover a greater distance (at least 5 mm) on the outer surface of the prosthesis body and is there available for irrigation.

In the case of hip joint spacers with irrigation liquid intake openings and irrigation liquid discharge openings for producing a proximal and a distal circuit for the irrigation liquid, provision may be made for the at least one first irrigation liquid discharge opening and the at least one first irrigation liquid intake opening to be demarcated from the at least one fastening area by at least one peripheral rib extending up out of the surface of the prosthesis body.

If the hip joint spacer is correctly applied, this may prevent the first and the second connectors and the irrigation liquid inlet opening and the irrigation liquid outlet opening and the at least one first irrigation liquid discharge opening and the at least one first irrigation liquid intake opening from being covered with bone cement and their functions thereby being impaired. It is in particular possible to prevent the hardened bone cement from preventing the first and second connectors from being pulled away or detached from the prosthesis body.

Provision may moreover be made for at least one irrigation liquid discharge opening of the at least one second irrigation liquid discharge opening and at least one irrigation liquid intake opening of the at least one second irrigation liquid intake opening to be arranged on the ball head next to the sliding surface, preferably on the ball head within 5 mm of the sliding surface.

This provisoin ensures that the at least one second irrigation liquid discharge opening and the at least one second irrigation liquid intake opening do not impair functioning of the sliding surface. In addition, in this way mechanical loading and associated undesired abrasion of the edges of the at least one second irrigation liquid discharge opening and of the at least one second irrigation liquid intake opening may be prevented.

Provision may moreover be made for at least one of the at least one first irrigation liquid discharge opening to be arranged at the end of the stem and for at least one of the at least one first irrigation liquid intake opening to be arranged on the distal side of the stem, at the point of transition from the collar to the stem or on the proximal side of the stem.

In this way, it is ensured that the irrigation liquid can irrigate the entire length of the stem with the medical irrigation liquid on the distal side of the prosthesis body, such that thorough irrigation of the femur may also proceed to the achievable depth.

Provision may moreover be made for the at least one irrigation liquid discharge opening inside the prosthesis body not to be connected in a liquid-conveying manner to the irrigation liquid outlet opening and for the at least one irrigation liquid intake opening inside the prosthesis body not to be connected in a liquid-conveying manner to the irrigation liquid inlet opening.

It is thereby ensured that a circuit with the irrigation liquid can be produced with the hip joint spacer without the irrigation liquid having first to be injected and then removed by suction. The hip joint spacer may also alternatively be used in such a way, however, that the irrigation liquid is first introduced into the hip joint spacer and exits through the at least one irrigation liquid discharge opening (preferably through the at least one first irrigation liquid discharge opening and the at least one second irrigation liquid discharge opening) and through the at least one irrigation liquid intake opening (preferably through the at least one first irrigation liquid intake opening and the at least one second irrigation liquid intake opening) and the irrigation liquid is then removed again by suction and in the process is sucked in through the at least one irrigation liquid discharge opening and the at least one irrigation liquid intake opening back into the prosthesis body.

Provision may further be made for the at least one irrigation liquid discharge opening and the at least one irrigation liquid intake opening to be spaced from one another, wherein the distance amounts to at least 5 mm, preferably at least 20 mm and particularly preferably at least 30 mm.

In this way, it is ensured that the medical irrigation liquid circuit has to cover a greater distance (at least 5 mm) on the outer surface of the prosthesis body and is there available for irrigation.

According to one preferred further development of the hip joint spacer according to the invention, provision may be made for the first connector on the side remote from the connection with the irrigation liquid inlet opening and the second connector on the side remote from the connection with the irrigation liquid outlet opening in each case to have an adapter, in particular in each case a Luer Lock adapter.

In this way, the hip joint spacer may be connected comfortably to a medical irrigation liquid reservoir with a pump and to a collecting vessel for receiving the used irrigation liquid.

Provision may also be made for a self-sealing coupling to be arranged at the irrigation liquid inlet opening inside the prosthesis body or at the surface of the prosthesis body and for a self-sealing coupling to be arranged at the irrigation liquid outlet opening inside the prosthesis body or at the surface of the prosthesis body, wherein the first connector is detachably connected or connectable to the irrigation liquid inlet opening and the second connector is detachably connected or connectable to the irrigation liquid outlet opening.

In this way, the irrigation liquid inlet opening and the irrigation liquid outlet opening or the liquid ducts therebehind close automatically if the first connector or the second connector is pulled away or separated from the prosthesis body. In this way, the passage is closed once no more irrigation liquid is to be passed through the hip joint spacer.

Provision may furthermore be made for the irrigation liquid inlet opening to be a first irrigation liquid inlet opening and for the irrigation liquid outlet opening to be a first irrigation liquid outlet opening, wherein a second irrigation liquid inlet opening and a second irrigation liquid outlet opening are additionally provided in the surface of the prosthesis body, wherein a self-sealing coupling is in each case arranged at the first irrigation liquid inlet opening, the second irrigation liquid inlet opening, the first irrigation liquid outlet opening and the second irrigation liquid outlet opening, wherein the first connector is detachably connectable in a liquid-tight manner to the first irrigation liquid inlet opening and to the second irrigation liquid inlet opening and the second connector is detachably connectable in a liquid-tight manner to the first irrigation liquid outlet opening and to the second irrigation liquid outlet opening and wherein the first irrigation liquid inlet opening and the second irrigation liquid inlet opening are connected with one another in a liquid-conveying manner in the prosthesis body and the first irrigation liquid outlet opening and the second irrigation liquid outlet opening are connected with one another in a liquid-conveying manner in the prosthesis body.

In this way, access to the hip joint spacer may be variably selected and adapted individually and in a patient-specific manner to the respective situation.

Provision may preferably also be made for the sum of the cross-sectional areas of all of the at least one irrigation liquid intake opening together to be at least as great as the cross-sectional area of the irrigation liquid inlet opening and/or the sum of all of the cross-sectional areas of the at least one irrigation liquid discharge opening to be at least as great as the cross-sectional area of the irrigation liquid outlet opening.

In this way, a dynamic pressure inside the prosthesis body may be avoided.

Provision may preferably further be made for the at least one irrigation liquid discharge opening and the at least one irrigation liquid intake opening not to be arranged in the sliding surface of the ball head.

This provison ensures that the at least one irrigation liquid discharge opening and the at least one irrigation liquid intake opening do not impair functioning of the sliding surface. In addition, in this way mechanical loading and associated undesired abrasion of the edges of the at least one irrigation liquid discharge opening and of the at least one irrigation liquid intake opening may be prevented.

Provision may furthermore be made for a first valve element to be arranged in the first connector or in the irrigation liquid inlet opening, the valve element preventing backflow of the irrigation liquid into the first connector, and/or for a second valve element to be arranged in the second connector or in the irrigation liquid outlet opening, the valve element preventing backflow of the irrigation liquid into the second connector, wherein the first and/or the second valve elements are preferably selected from a non-return valve, a ball valve with spring, a lip valve, a Bunsen valve or a plate valve.

This provision makes it possible to predefine a circulating circuit of the medical irrigation liquid. In addition, backflow of the medical irrigation liquid used is thus prevented.

A preferred further development of the present invention proposes arranging a first valve in a first duct inside the prosthesis body which connects the at least one irrigation liquid intake opening in a liquid-conveying manner to the irrigation liquid outlet opening, the first valve being openable solely by applying a vacuum at the irrigation liquid outlet opening and preventing backflow of the irrigation liquid into the first duct, and/or arranging a second valve in a second duct inside the prosthesis body which connects the at least one irrigation liquid discharge opening in a liquid-conveying manner to the irrigation liquid inlet opening, the second valve being openable solely by applying a vacuum at the irrigation liquid inlet opening and preventing backflow of the irrigation liquid into the second duct.

Backflow of the medical irrigation liquid may thereby also be prevented. It may additionally be ensured in this way that an exchange of contained irrigation liquid with surrounding liquids still takes place without the connector.

Provision may also be made for the irrigation liquid inlet opening, the irrigation liquid outlet opening, the at least one irrigation liquid discharge opening and the at least one irrigation liquid intake opening and the liquid-conveying connections to be formed in the prosthesis body, wherein the prosthesis body is preferably made of plastic, metal, ceramic, glass ceramic, bone cement or a combination thereof.

A compact structure is thereby achieved and the prosthesis body externally resembles a conventional femoral hip joint spacer, apart from the openings.

Provision may moreover be made for the irrigation liquid inlet opening and the irrigation liquid outlet opening to be arranged in a lateral surface of the neck, in the distal side of the ball head or of the collar, in particular in the proximal side of the collar.

This provision makes feed and drainage of the irrigation liquid into and out of the hip joint spacer anatomically easy and comfortable to put in place. At the lateral side surface, the connector connected to the irrigation liquid inlet opening and the irrigation liquid outlet opening are particularly untroublesome during walking and are also particularly readily accessible.

Provision may preferably furthermore be made for at least one irrigation liquid discharge opening of the at least one irrigation liquid discharge opening to be arranged at the end of the stem.

This provision ensures that the irrigation liquid can also irrigate the end of the stem with the medical irrigation liquid, such that thorough irrigation of the femur may also proceed to the achievable depth.

Provision may furthermore be made for the prosthesis body to be of a multipart configuration and to have a stem part and at least one head part, which are detachably connectable or connected with one another via a connector, in particular via a screw connection, the prosthesis body preferably having a stem part and a plurality of head parts, wherein the head parts have ball heads of different diameters.

In this way, a variable hip joint spacer adaptable to different treatment situations is provided.

The invention is based on the surprising recognition that a temporary hip joint spacer may be used for continuous irrigation of a cavity in the body of a patient in that, at the surface of the prosthesis body of the hip joint spacer and inside the prosthesis body, suitable openings and ducts for the irrigation liquid are respectively present and in that two externally accessible connectors are connected or connectable, through which the medical irrigation liquid may be fed from outside into the prosthesis body and the used irrigation liquid may be drained back out of the prosthesis body. With the hip joint spacer, in a preferred embodiment both a distal and a proximal side may be irrigated by separate circuits of irrigation liquid, such that the collar of the hip joint spacer, which is used to rest against the femur, does not have to be flowed around by the irrigation liquid.

The hip joint spacer according to the invention may advantageously be used in the context of two-stage septic revisions, in which an infection with two or more microbial microorganisms and in particular with problematic microorganisms is present. It is particularly advantageous for the hip joint spacer and the surrounding soft tissue and at least in part also the surrounding bone tissue to be irrigated with antibiotically active solutions, such as antibiotics and also antiseptics or in specific cases with antimycotics, wherein the type and number of the active ingredients and above all the concentration of the antimicrobial active ingredients in the irrigation solution (the medical irrigation liquid) may be precisely adjusted. By suctioning the irrigation liquid away, it is also possible for the residence time of the antimicrobial irrigation liquid in the patient to be precisely adjusted. This precise adjustment makes it possible to ensure irrigation around the surface of the hip joint spacer for several days with precisely pre-adjusted concentrations of antimicrobial active ingredients in the irrigation liquid. In this way, protection from microbial recolonization of the surfaces of the hip joint spacer is markedly reduced compared with the hip joint spacers hitherto made from antibiotic-containing bone cement. After antibiotic irrigation, it is possible to irrigate the surface of the hip joint spacer and of the surrounding tissue with active ingredient-free irrigation liquids, thereby removing residues of the antimicrobial active ingredients. The development of resistance as a result of persistent active ingredient residues is therefore extremely unlikely.

It is moreover advantageous for the irrigation liquids also to be able to contain antimicrobial active ingredients which cannot normally be integrated into the hip joint spacers made from bone cement because they would disturb or prevent free-radical polymerization of the bone cement paste. The active ingredients rifampicin and metronidazole are examples thereof.

When the clinical parameters reveal that the infection or inflammation is receding, then the connectors may be removed from the hip joint spacer. The connectors are to this end advantageously connected by an external thread or via a bayonet closure or via a plug-type closure to the irrigation liquid inlet opening and the irrigation liquid outlet opening, or in each case by a mating fastening element, matching the fastening element on the connectors, in or on the irrigation liquid inlet opening and the irrigation liquid outlet opening.

Provision may preferably be made for the irrigation liquid inlet opening and the irrigation liquid outlet opening to terminate flush with the surface of the hip joint spacer once the connectors have been removed, in order to prevent irritation of the surrounding soft tissue.

An exemplary hip joint spacer according to the invention may be composed of:

A) a ball head with a sliding surface,
B) a neck which is connected to the ball head,
C) a collar, the proximal side of which is connected to the neck,
D) a stem, which is connected to the distal side of the collar,
E) at least one irrigation liquid inlet opening above the distal side of the collar, which is detachably connected in a liquid-conveying manner to a first connector,
F) at least one irrigation liquid outlet opening on or above the proximal side of the collar, which is connected in a liquid-conveying manner to the irrigation liquid inlet opening,
G) at least one irrigation liquid outlet opening, which is arranged on or below the distal side of the collar, wherein the irrigation liquid outlet opening is connected in a liquid-conveying manner to the irrigation liquid inlet opening,
H) at least one irrigation liquid receiving opening, which is arranged on or above the distal side of the collar, wherein the irrigation liquid receiving opening is connected in a liquid-conveying manner to a second connector,
I) at least one irrigation liquid outlet opening, which is arranged on or above the proximal side of the collar, wherein the at least one irrigation liquid outlet opening is connected in a liquid-conveying manner to the irrigation liquid receiving opening,
J) at least one irrigation liquid outlet opening, which is arranged on or below the distal side of the collar, wherein this at least one irrigation liquid outlet opening is connected in a liquid-conveying manner to the irrigation liquid receiving opening, and
K) at least one fastening area on the proximal stem, provided for cementing, which is demarcated by a peripheral rib.

The fastening area provided for cementing preferably has at most an extent which is smaller than the external diameter of the stem.

The distance between the mutually associated irrigation liquid discharge openings and the irrigation liquid intake openings amounts to at least 0.5 cm, preferably at least 2.0 cm and most preferably at least 3.0 cm. This configuration allows irrigation of the surface of the hip joint spacer by the irrigation liquid before the irrigation liquid is removed again by suction through the irrigation liquid intake openings.

Provision may also be made according to the invention for the irrigation liquid inlet opening and the irrigation liquid outlet opening to be arranged in the neck or in the collar next to the sliding surface of the ball head. In this way, the connector may be guided on the shortest path from the hip joint spacer outwards through the body surface.

The sum of the cross-sections of the irrigation liquid intake openings is preferably greater than or equal to the cross-section of the irrigation liquid discharge openings.

Provision may also be made according to the invention for a non-return valve to be arranged between the at least one irrigation liquid intake opening and the irrigation liquid outlet opening, the valve preventing backflow of the irrigation liquid out of the second connector into the prosthesis body, wherein a ball valve with a spring, a lip valve, a Bunsen valve and a plate valve are preferred as the non-return valve.

A non-return valve is advantageously arranged in a duct inside the prosthesis body, the valve preventing backflow of the irrigation liquid out of the irrigation liquid inlet opening into the first connector, wherein a ball valve with a spring, a lip valve, a Bunsen valve and a plate valve are preferred as the non-return valve.

According to the invention, a suction valve is arranged in a duct inside the prosthesis body, the valve preventing backflow of the irrigation liquid into the at least one irrigation liquid outlet opening, wherein a ball valve with a spring, a lip valve, a Bunsen valve and a plate valve are preferred as the suction valve.

The hip joint spacer may be made of plastic, metal, ceramic, glass ceramic and combinations thereof. The spacer may advantageously be made from a metal core, produced by SLM (Selective Laser Melting), and a casing of bone cement arranged therearound. It is also possible to make the entire hip joint spacer of metal, such as for example stainless steel and titanium alloys, by SLM. Stainless steel 1.4404 and titanium alloy $Ti_6Al_4V$ are preferred in this case.

It is to be understood that both the foregoing general description and the following detailed description are exemplary, but are not restrictive, of the disclosure.

BRIEF DESCRIPTION OF THE DRAWING

The disclosure is best understood from the following detailed description when read in connection with the accompanying drawing. Further exemplary embodiments of the invention are explained below with reference to twenty-two schematically depicted figures, but without thereby restricting the invention. In the figures.

DETAILED DESCRIPTION OF THE DISCLOSURE

Figure 1:
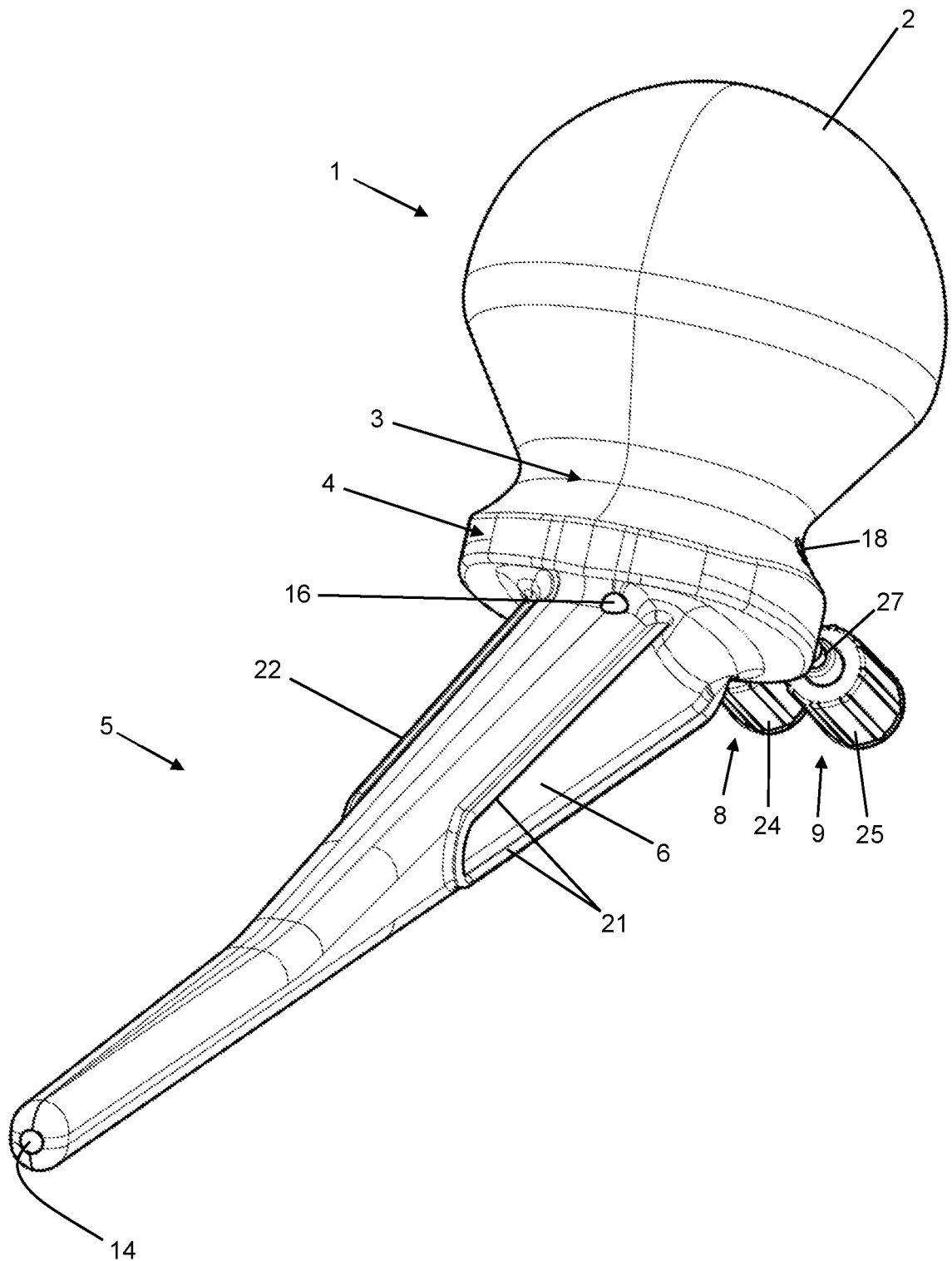
FIG. 1 is a schematic perspective external view of a first exemplary hip joint spacer according to the invention with an irrigation device.
Figure 2:
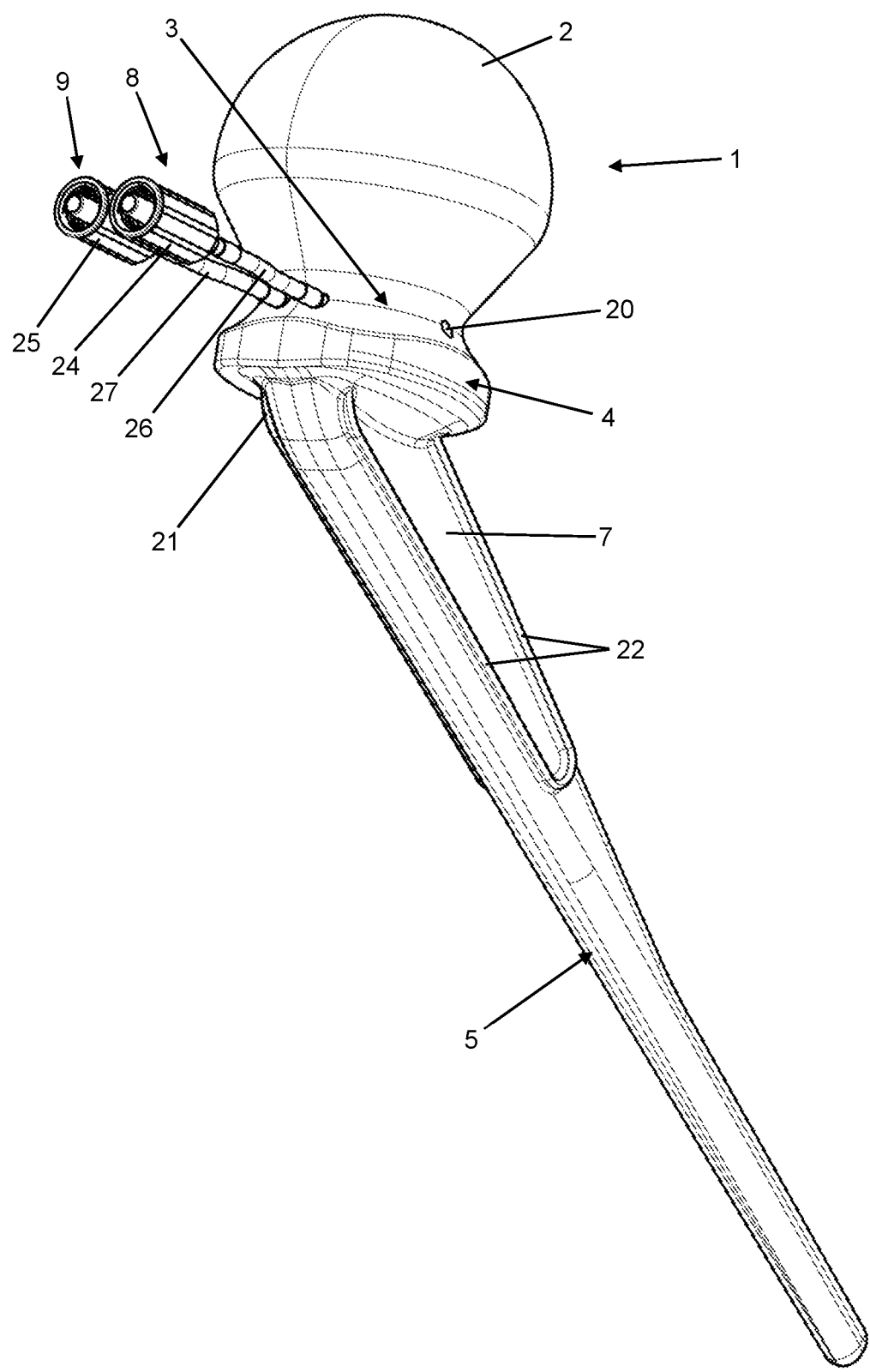
FIG. 2 is a schematic perspective external view of the first hip joint spacer according to the invention illustrated in FIG. 1 but onto the opposite side.
Figure 3:
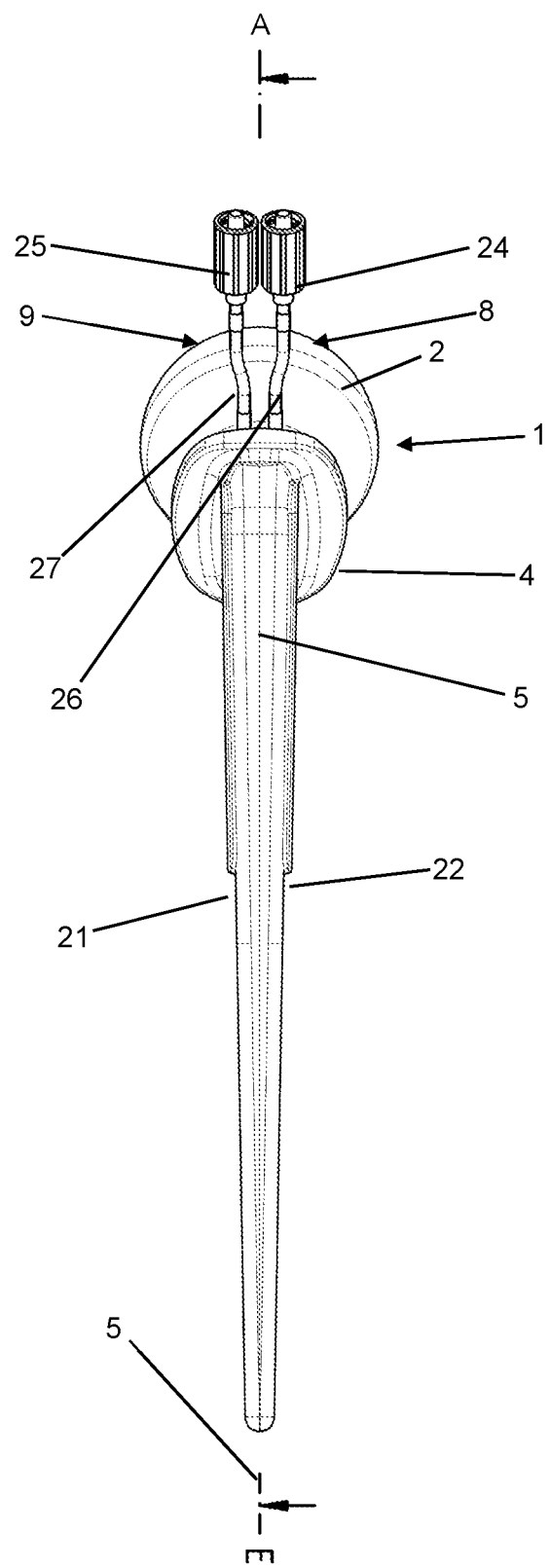
FIG. 3 is a schematic perspective external view of the first hip joint spacer according to the invention illustrated in FIGS. 1 and 2 but onto a further side.

FIGS. 1 to 7 show depictions of a first exemplary embodiment of a hip joint spacer according to the invention with an irrigation device. The femoral hip joint spacer (i.e., the hip joint spacer replicating the joint head of the femur and intended to be fastened to the femur) has a ball head 1 with a sliding surface 2 on the proximal side. The sliding surface 2 lies when inserted (i.e., when inserted into the patient) against the hip joint socket and so forms part of the hip joint. On the distal side opposite the sliding surface 2, the ball head 1 is connected to a collar 4 via a neck 3. The neck 3 is thinner than the ball head 1 and the collar 4. On the distal side of the collar 4 a stem 5 is attached, which extends in the distal direction and serves in fastening the hip joint spacer in the femur. To this end, the hip joint spacer has fastening areas 6, 7 on two opposing sides of the stem 5, these being provided to connect the hip joint spacer to the femur with the aid of bone cement paste. The ball head 1, the neck 3, the collar 4 and the stem 5 form a prosthesis body of the hip joint spacer. The prosthesis body largely corresponds in its external shape to the external shape of known hip joint spacers.

Unlike with known hip joint spacers, on one side of the first exemplary hip joint spacer a first tubular connector 8 is fastened to an irrigation liquid inlet opening and a second tubular connector 9 is fastened to an irrigation liquid outlet opening. The irrigation liquid inlet opening and the irrigation liquid outlet opening lead into the inside of the prosthesis body and are arranged in the region of the neck 3. The first tubular connector 8 and the second tubular connector 9 are liquid-conveying, such that a medical irrigation liquid can be passed through the first tubular connector 8 into the prosthesis body and a liquid can be drained out of the prosthesis body through the second tubular connector 9. The first connector 8 and the second connector 9 are connected detachably to the irrigation liquid inlet opening and the irrigation liquid outlet opening.

At the distal end of the stem 5 a first irrigation liquid discharge opening 14 is arranged and at the point of transition from the stem 5 to the collar 4 a first irrigation liquid intake opening 16 is arranged. Furthermore, a second irrigation liquid intake opening 18 is arranged on the neck 3 or at the point of transition from the neck 3 to the collar 4 and a second irrigation liquid discharge opening 20 is arranged on the opposite side from the second irrigation liquid intake opening 18 on the neck 3 or at the point of transition from the neck 3 to the collar 4. The first irrigation liquid discharge opening 14 and the first irrigation liquid intake opening 16 are thereby arranged on the distal side of the hip joint spacer and the second irrigation liquid discharge opening 20 and the second irrigation liquid intake opening 18 are arranged on the proximal side of the hip joint spacer, wherein the proximal and distal sides are separated by the collar 4. The first irrigation liquid discharge opening 14 and the first irrigation liquid intake opening 16 on the one hand and the second irrigation liquid discharge opening 20 and the second irrigation liquid intake opening 18 on the other hand are thereby suited to forming two medical irrigation liquid circuits, separated by the collar 4, along the distal and proximal surfaces of the hip joint spacer.

The fastening areas 6, 7 are each delimited by a peripheral rib 21, 22 and at the proximal sides of the fastening areas 6, 7 by the collar 4. The ribs 21, 22 extend up out of the surface of the stem 5 and reach as far as the collar 4. The ribs 21, 22 should be understood as being part of the prosthesis body. The purpose of the projecting ribs 21, 22 and the collar 4 is to prevent bone cement paste from reaching, or at least hinder the paste from reaching, outside the fastening areas 6, 7 on fastening of the hip joint spacer to the femur and thereby closing or impeding the first irrigation liquid discharge opening 14, the first irrigation liquid intake opening 16, the second irrigation liquid discharge opening 20, the second irrigation liquid intake opening 18 or the irrigation liquid inlet opening and the irrigation liquid outlet opening or undesirably cementing firm the first connector 8 or the second connector 9 on the prosthesis body.

The first connector 8 has a Luer Lock adapter 24 and a short, flexible hose 26. The second connector 9 likewise has a Luer Lock adapter 25 and a short, flexible hose 27. In this way, the hip joint spacer may be connected by the first connector 8 via the Luer Lock adapter 24 to a source of a medical irrigation liquid with a pump (not shown) and the second connector 9 via the Luer Lock adapter 25 to a collecting vessel and optionally likewise a pump (not shown).

Figure 4:
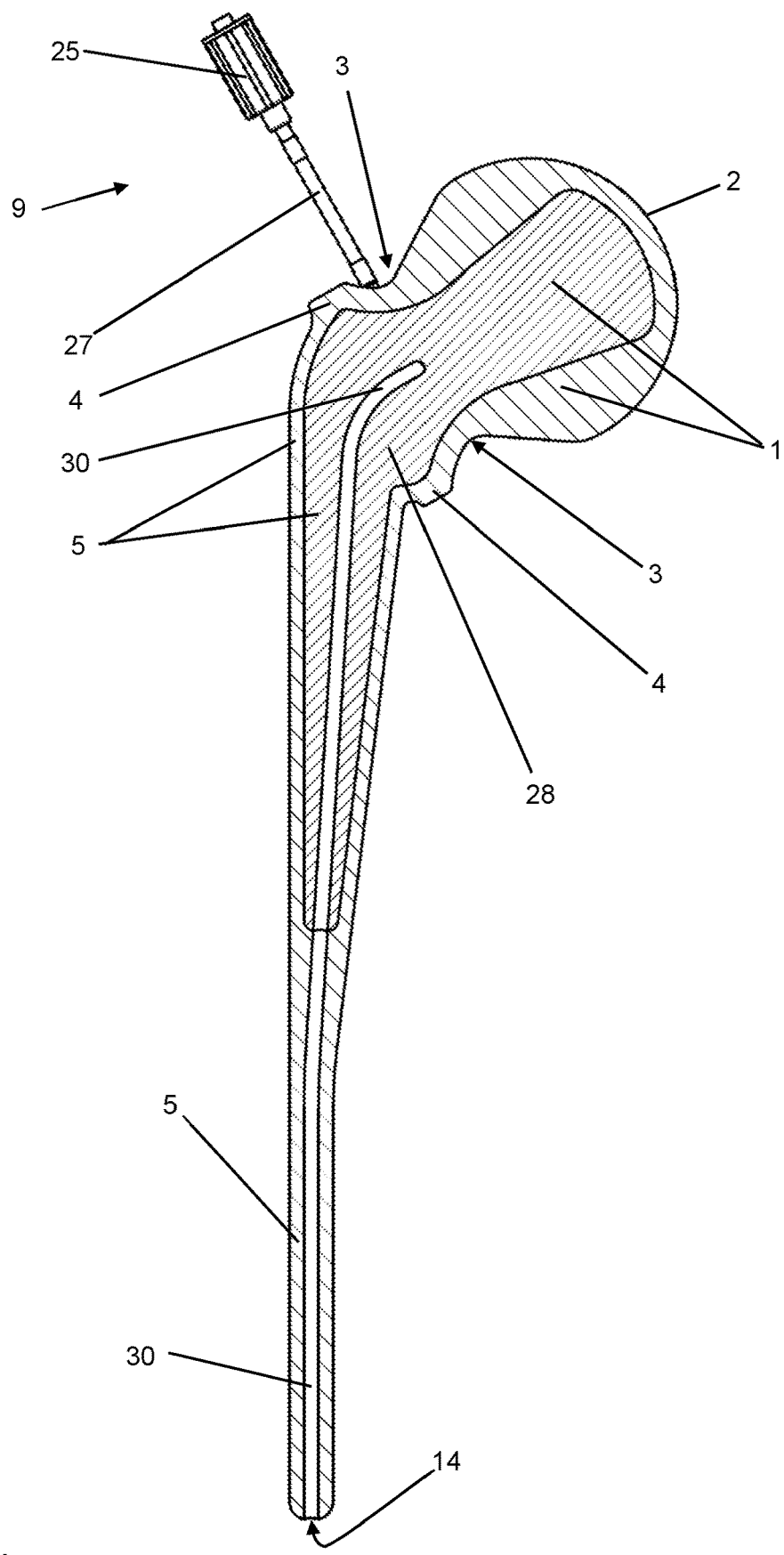
FIG. 4 is a schematic cross-sectional view of the first hip joint spacer according to the invention corresponding to section A in FIG. 3.
Figure 5:
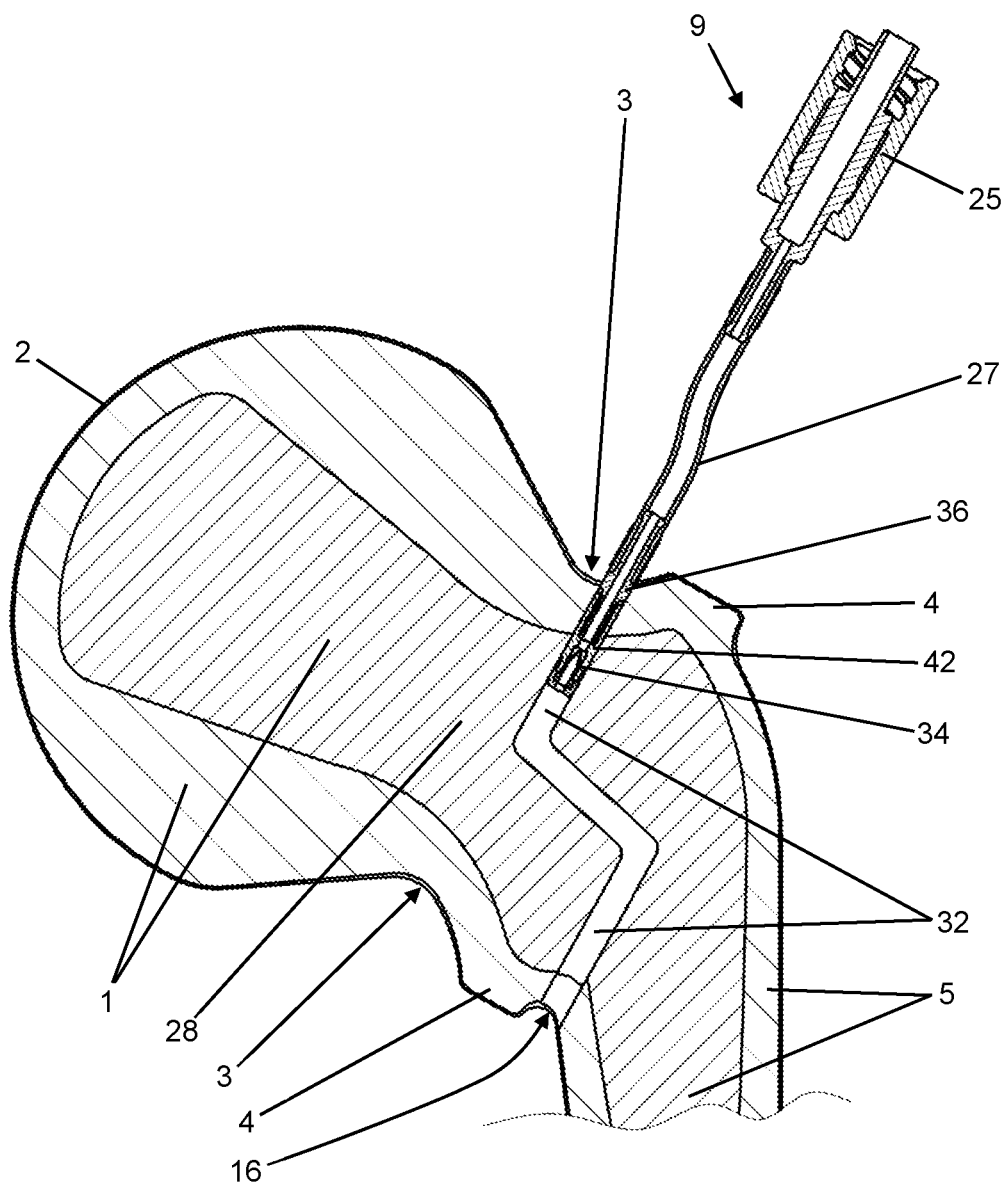
FIG. 5 is a schematic cross-sectional view through a portion of the first hip joint spacer according to the invention, wherein the section plane extends parallel to section A according to FIG. 3.
Figure 6:
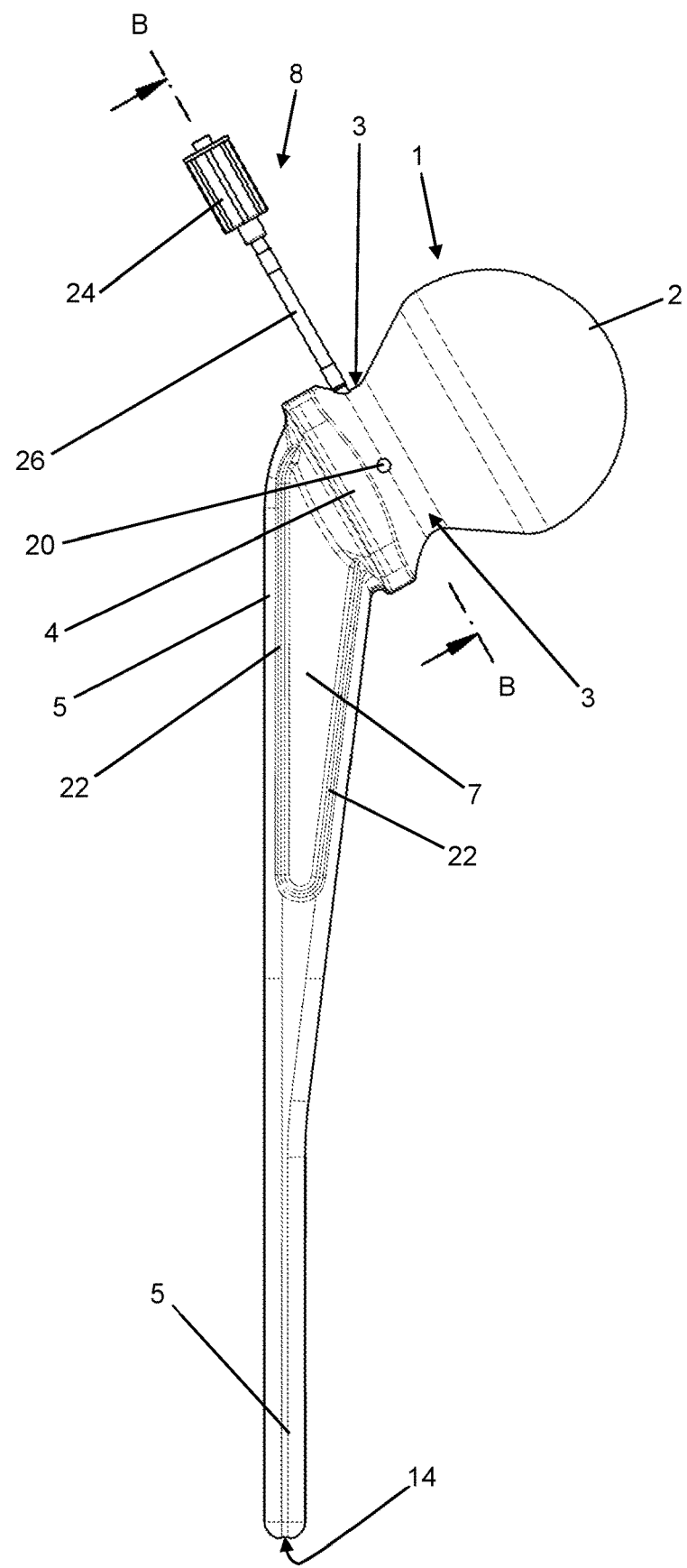
FIG. 6 is a schematic side view of the first hip joint spacer according to the invention illustrated in FIGS. 1 to 5, wherein the direction of view corresponds to the cross-sectional view according to FIG. 4.
Figure 7:
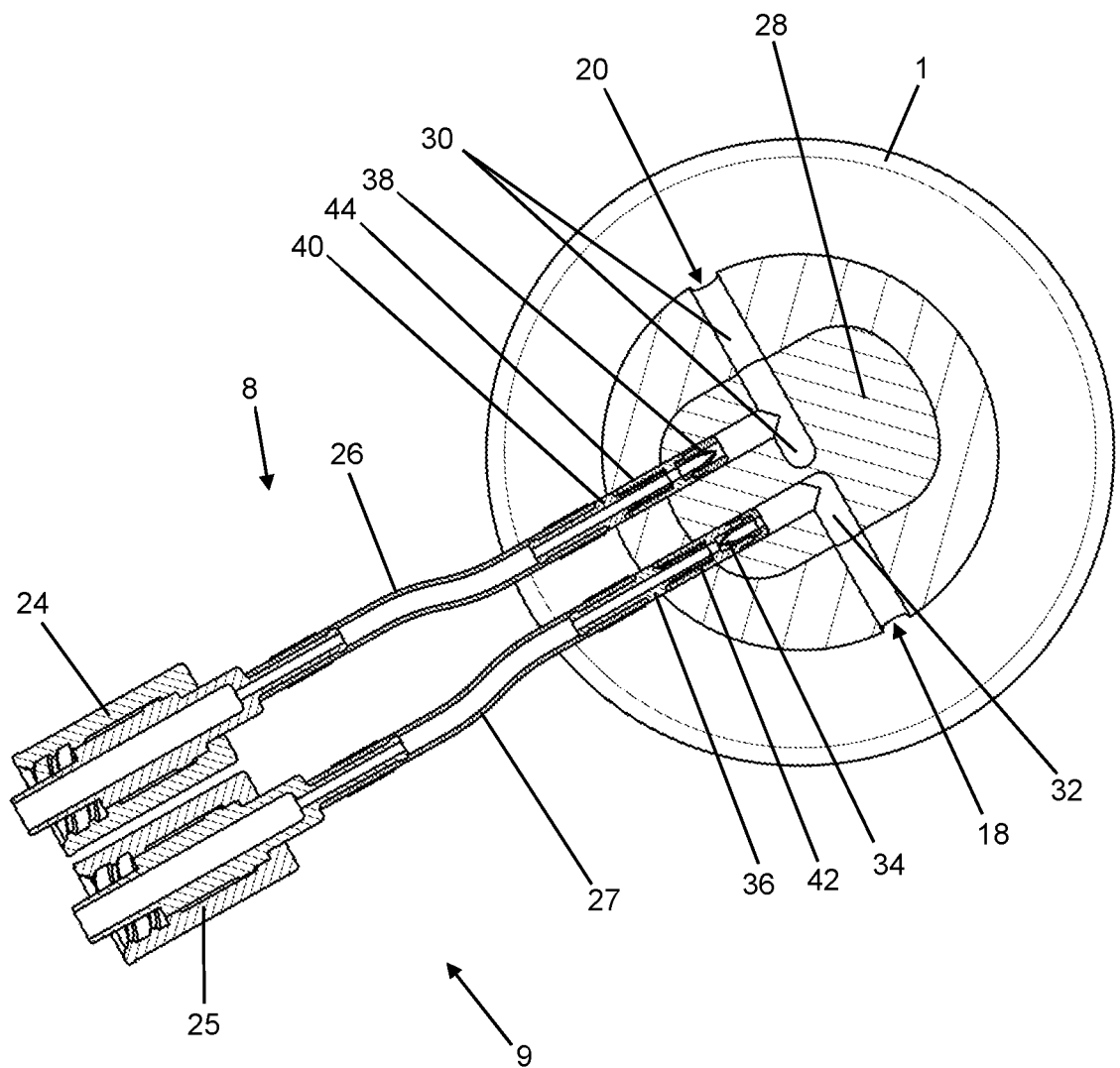
FIG. 7 is a schematic cross-sectional view of the first hip joint spacer according to the invention corresponding to section B in FIG. 6, wherein the section plane extends perpendicular to the section planes of FIGS. 4 and 5.
Figure 8:
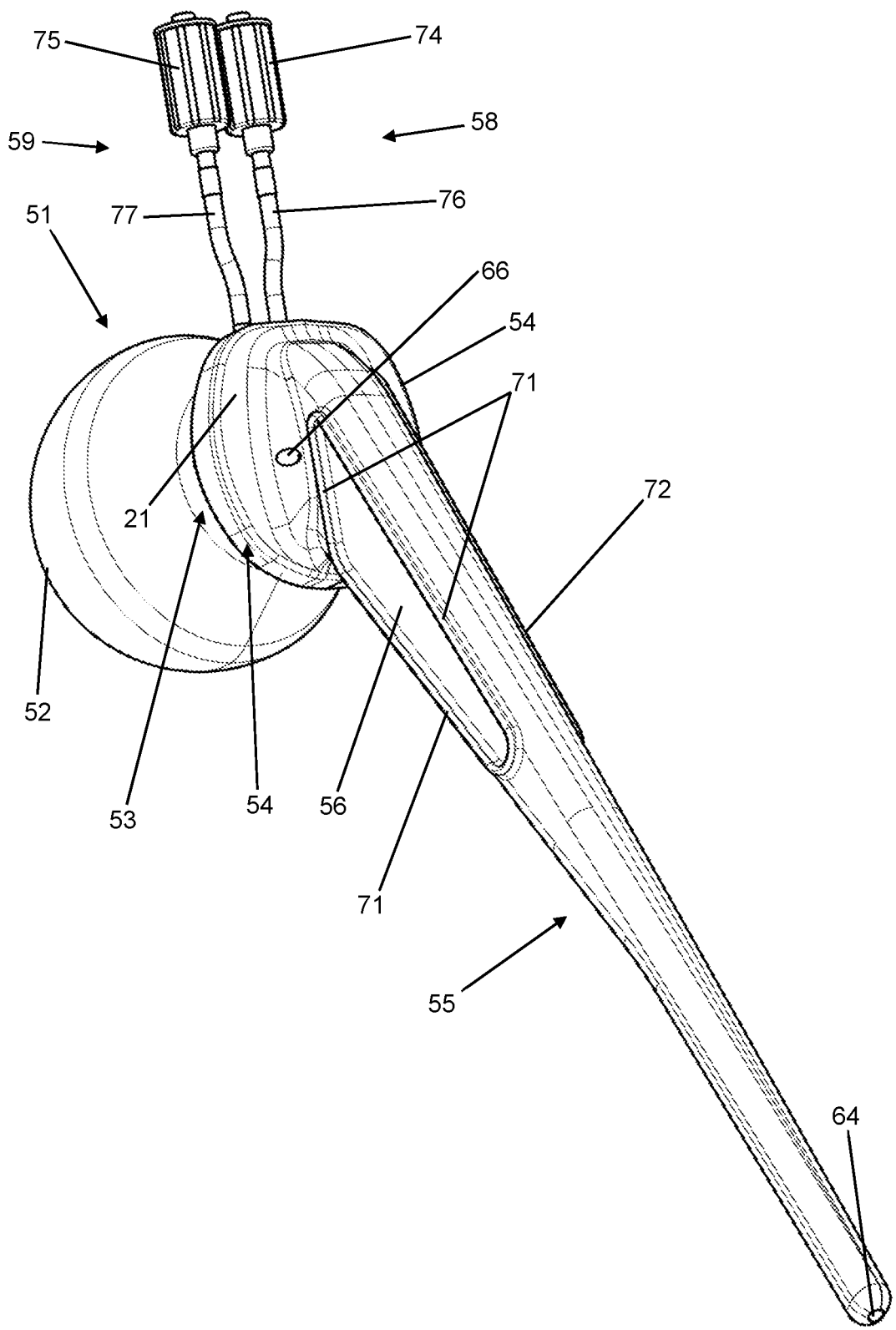
FIG. 8 is a schematic perspective external view of a second hip joint spacer according to the invention with an irrigation device.
Figure 9:
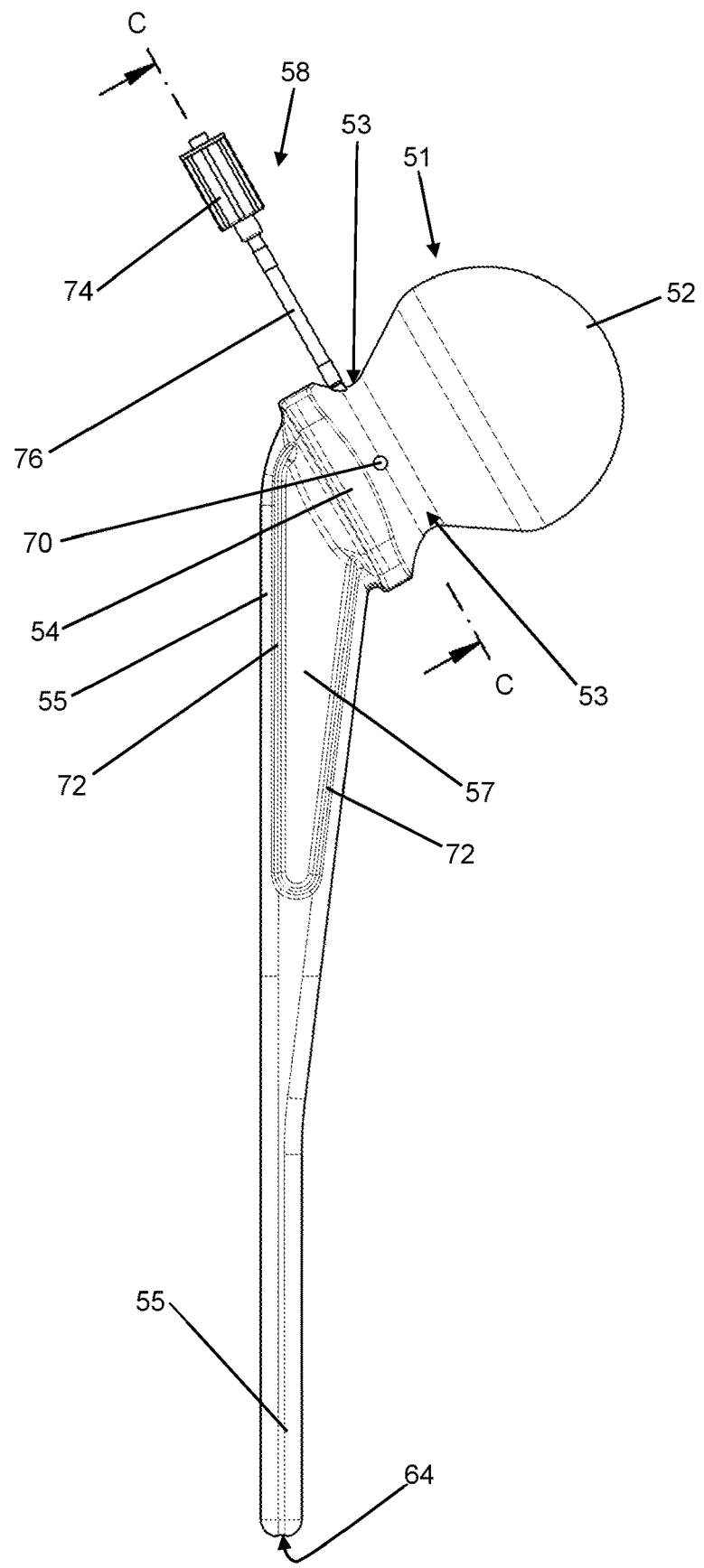
FIG. 9 is a schematic side view of the second hip joint spacer according to the invention illustrated in FIG. 8.

In the cross-sectional views according to FIGS. 4, 5 and 7, it is apparent how the irrigation liquid outlet opening is connected to the first irrigation liquid intake opening 16 and to the second irrigation liquid intake opening 18 and the irrigation liquid inlet opening is connected to the first irrigation liquid discharge opening 14 and to the second irrigation liquid discharge opening 20 inside the prosthesis body. The cross-sectional views further show that the hip joint spacer has a core 28 of a metal, while the outer regions of the prosthesis body are made substantially of a plastic material, preferably of a bone cement, such as a PMMA plastic, which may be loaded with an antibiotic or with a plurality of antibiotics.

Inside the prosthesis body the irrigation liquid inlet opening is connected to the first irrigation liquid discharge opening 14 and the second irrigation liquid discharge opening 20 via a first duct 30. The duct 30 produces a liquid-conveying connection between the irrigation liquid inlet opening and the first irrigation liquid discharge opening 14 and the second irrigation liquid discharge opening 20. To this end, inside the prosthesis body, in the region of the cross-section at the neck 3, a branch in the form of a T-piece is present in the first duct 30. Likewise, inside the prosthesis body the irrigation liquid outlet opening is connected to the first irrigation liquid intake opening 16 and the second irrigation liquid intake opening 18 via a second duct 32. For this purpose, the second duct 32 also comprises a branch. The first duct 30 and the second duct 32 are separated from one another inside the prosthesis body.

A valve element 34 is provided in the second duct 32, directly in front of the irrigation liquid outlet opening, the valve element 34 allowing outflow of liquid from the second duct 32 through the irrigation liquid outlet opening out of the prosthesis body into the second connector 9 and preventing backflow from the second connector 9 into the second duct 32. The second connector 9 is connected to the irrigation liquid outlet opening via a detachable connecting element 36.

A valve element 38 is provided in the first duct 30, directly in front of the irrigation liquid inlet opening, the valve element 38 allowing inflow of the medical irrigation liquid into the first duct 30 through the irrigation liquid inlet opening into the prosthesis body and preventing backflow from the first duct 30 into the first connector 8. The first connector 8 is connected to the irrigation liquid inlet opening via a detachable connecting element 40.

The first connector 8 and the second connector 9 may be detached from the prosthesis body by pulling or screwing off the detachable connecting elements 36, 40. To this end, liquid-conveying mating fastening elements 42, 44 are provided in the ducts 30, 32 in the prosthesis body. The mating fastening elements 42, 44 may for example be made from sleeves with internal threads, into which the connecting elements 36, 40 in the form of liquid-conveying sleeves with external threads have been or can be screwed.

In the inserted state, the femoral hip joint spacer may be used as follows for irrigation. A medical irrigation liquid with a composition adapted to the patient's needs, such as for example a sterile Ringer's solution with a mixture of suitable antibiotics, is fed through the first connector 8 into the prosthesis body. The medical irrigation liquid flows through the valve element 38 and through the first duct 30 through the prosthesis body and exits through the first irrigation liquid discharge opening 14 and through the second irrigation liquid discharge opening 20 out of the prosthesis body. The irrigation liquid then flows along the surface of the hip joint spacer from the first irrigation liquid discharge opening 14 to the first irrigation liquid intake opening 16 and from the second irrigation liquid discharge opening 20 to the second irrigation liquid intake opening 18. The regions therebetween are irrigated with a film of the medical irrigation liquid. The used irrigation liquid re-enters the prosthesis body at the first irrigation liquid intake opening 16 and the second irrigation liquid intake opening 18 and flows through the second duct 32 and the valve element 38 to the irrigation liquid outlet opening. From there the used irrigation liquid is removed by suction from the prosthesis body through the second connector 9 and the used irrigation liquid is disposed of or collected.

If no further irrigation is to take place, the connectors 8, 9 with the connecting elements 36, 40 are separated from the prosthesis body and the remaining hip joint spacer may also be used like a normal hip joint spacer. Provision may preferably be made for the irrigation liquid inlet opening and the irrigation liquid outlet opening to close automatically on pulling or screwing the connecting elements 36, 40 off the prosthesis body.

As a variant of the first exemplary hip joint spacer, the distal irrigation liquid intake opening 16 and the proximal irrigation liquid discharge opening 20 could be closed. A single circuit of the irrigation liquid would thereby be produced via the distal irrigation liquid discharge opening 14 and the proximal irrigation liquid intake opening 18, the circuit extending both over the distal and over the proximal side of the hip joint spacer. The irrigation liquid has then to flow over the collar 4.

FIGS. 8 to 12 show depictions of a second exemplary embodiment of a hip joint spacer according to the invention with an irrigation device. The femoral hip joint spacer has a ball head 51 with a sliding surface 52 on the proximal side. The sliding surface 52 rests when inserted against the hip joint socket and thereby forms a part of the hip joint. On the distal side opposite the sliding surface 52, the ball head 51 is connected to a collar 54 via a neck 53. The neck 53 is thinner than the ball head 51 and the collar 54. On the distal side of the collar 54 a stem 55 is attached, which extends in the distal direction and serves in fastening the hip joint spacer in the femur. To this end, the hip joint spacer has fastening areas 56, 57 on two opposing sides of the stem 55, these being provided to connect the hip joint spacer to the femur with the aid of bone cement paste. The ball head 51, the neck 53, the collar 54 and the stem 55 form a prosthesis body of the hip joint spacer. The prosthesis body corresponds in this respect in its external shape to the first exemplary hip joint spacer according to FIGS. 1 to 7, apart from the smaller area of one fastening area 56.

On one side of the second exemplary hip joint spacer, a first tubular connector 58 is fastened to an irrigation liquid inlet opening 67 and a second tubular connector 59 is fastened to an irrigation liquid outlet opening 69. The irrigation liquid inlet opening 67 and the irrigation liquid outlet opening 69 lead into the inside of the prosthesis body and are arranged in the region of the neck 53. The first tubular connector 58 and the second tubular connector 59 are liquid-conveying, such that a medical irrigation liquid can be passed through the first tubular connector 58 into the prosthesis body and a liquid can be drained out of the prosthesis body through the second tubular connector 59. The first connector 58 and the second connector 59 are connected detachably to the irrigation liquid inlet opening 67 and the irrigation liquid outlet opening 69.

A first irrigation liquid discharge opening 64 is arranged at the distal end of the stem 55 and a first irrigation liquid intake opening 66 is arranged at the point of transition from the stem 55 to the collar 54 in the region between one of the fastening areas 56 and the collar 54. Furthermore, a second irrigation liquid intake opening 68 is arranged on the neck 53 or at the point of transition from the neck 53 to the collar 54 and a second irrigation liquid discharge opening 70 is arranged on the opposite side from the second irrigation liquid intake opening 68 on the neck 53 or at the point of transition from the neck 53 to the collar 54. The first irrigation liquid discharge opening 64 and the first irrigation liquid intake opening 66 are thereby arranged on the distal side of the hip joint spacer and the second irrigation liquid discharge opening 70 and the second irrigation liquid intake opening 68 are arranged on the proximal side of the hip joint spacer, wherein the proximal and distal sides are separated by the collar 54. The first irrigation liquid discharge opening 64 and the first irrigation liquid intake opening 66 on the one hand and the second irrigation liquid discharge opening 70 and the second irrigation liquid intake opening 68 on the other hand are thereby suited to forming two medical irrigation liquid circuits, separated by the collar 54, along the distal and proximal surfaces of the hip joint spacer.

Unlike in the first exemplary embodiment illustrated in FIGS. 1 to 7, one fastening area 56 is delimited completely by a peripheral rib 71, while the other fastening area 57 is delimited as in the first exemplary embodiment by a peripheral rib 72 and on the proximal side of the fastening area 57 by the collar 54. The ribs 71, 72 extend up out of the surface of the stem 55. The ribs 71, 72 should be understood as being part of the prosthesis body. The purpose of the projecting ribs 71, 72 and the collar 54 is to prevent bone cement paste from reaching, or at least hiinder the paste from reaching, outside the fastening areas 56, 57 on fastening of the hip joint spacer to the femur and thereby closing or impeding the first irrigation liquid discharge opening 64, the first irrigation liquid intake opening 66, the second irrigation liquid discharge opening 70, the second irrigation liquid intake opening 68 or the irrigation liquid inlet opening and the irrigation liquid outlet opening or undesirably cementing firm the first connector 58 or the second connector 59 on the prosthesis body. Unlike in the first exemplary embodiment, the second irrigation liquid intake opening 66 is arranged between the collar 54 and the fastening area 56 (as is readily apparent in FIG. 11).

The first connector 58 has a Luer Lock adapter 74 and a short, flexible hose 76. The second connector 59 likewise has a Luer Lock adapter 75 and a short, flexible hose 77. In this way, the hip joint spacer may be connected by the first connector 58 via the Luer Lock adapter 74 to a source of a medical irrigation liquid with a pump (not shown) and the second connector 59 via the Luer Lock adapter 76 to a collecting vessel and optionally likewise a pump (not shown).

Figure 10:
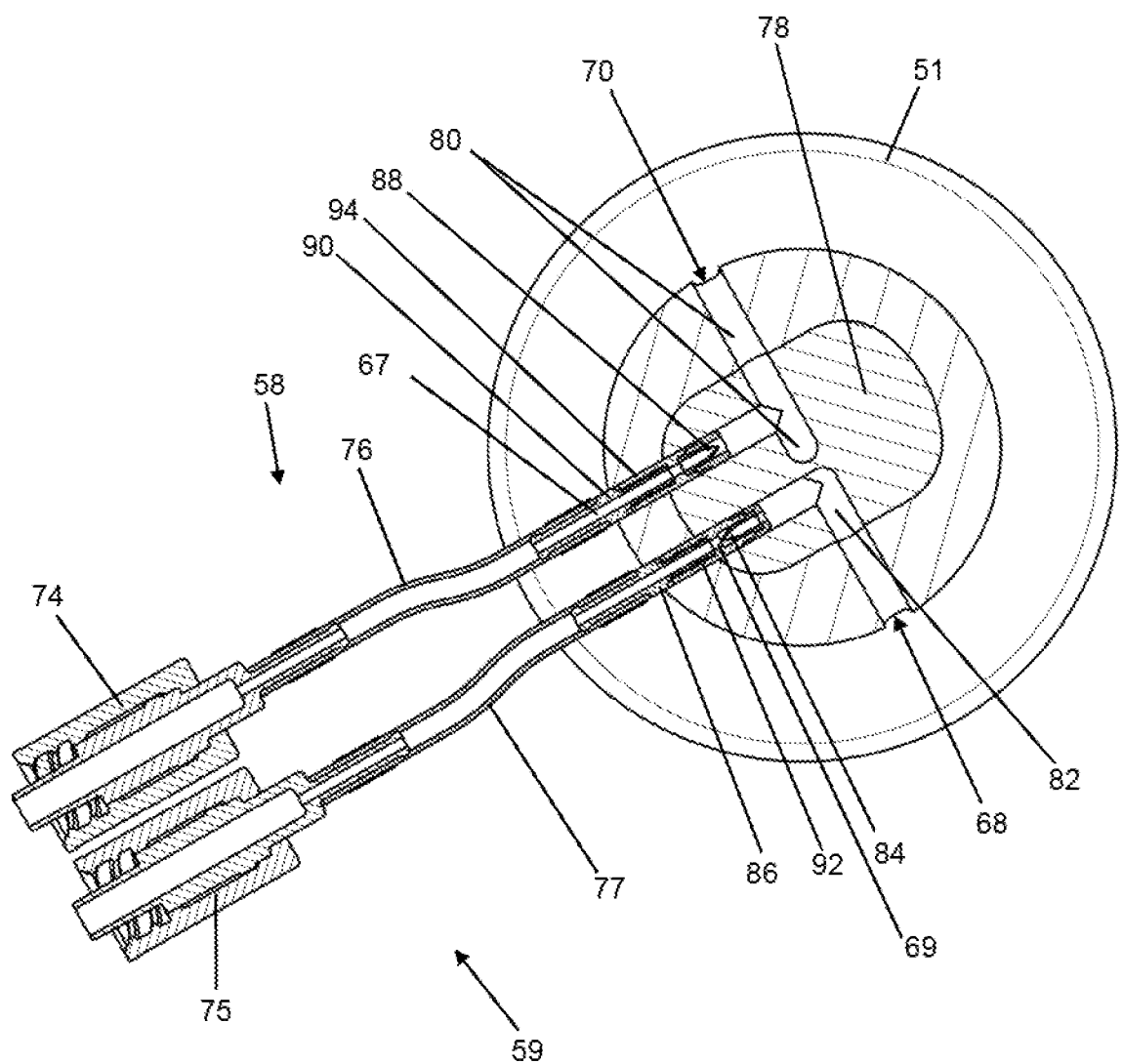
FIG. 10 is a schematic cross-sectional view of the second hip joint spacer according to the invention corresponding to section C in FIG. 9.
Figure 11:
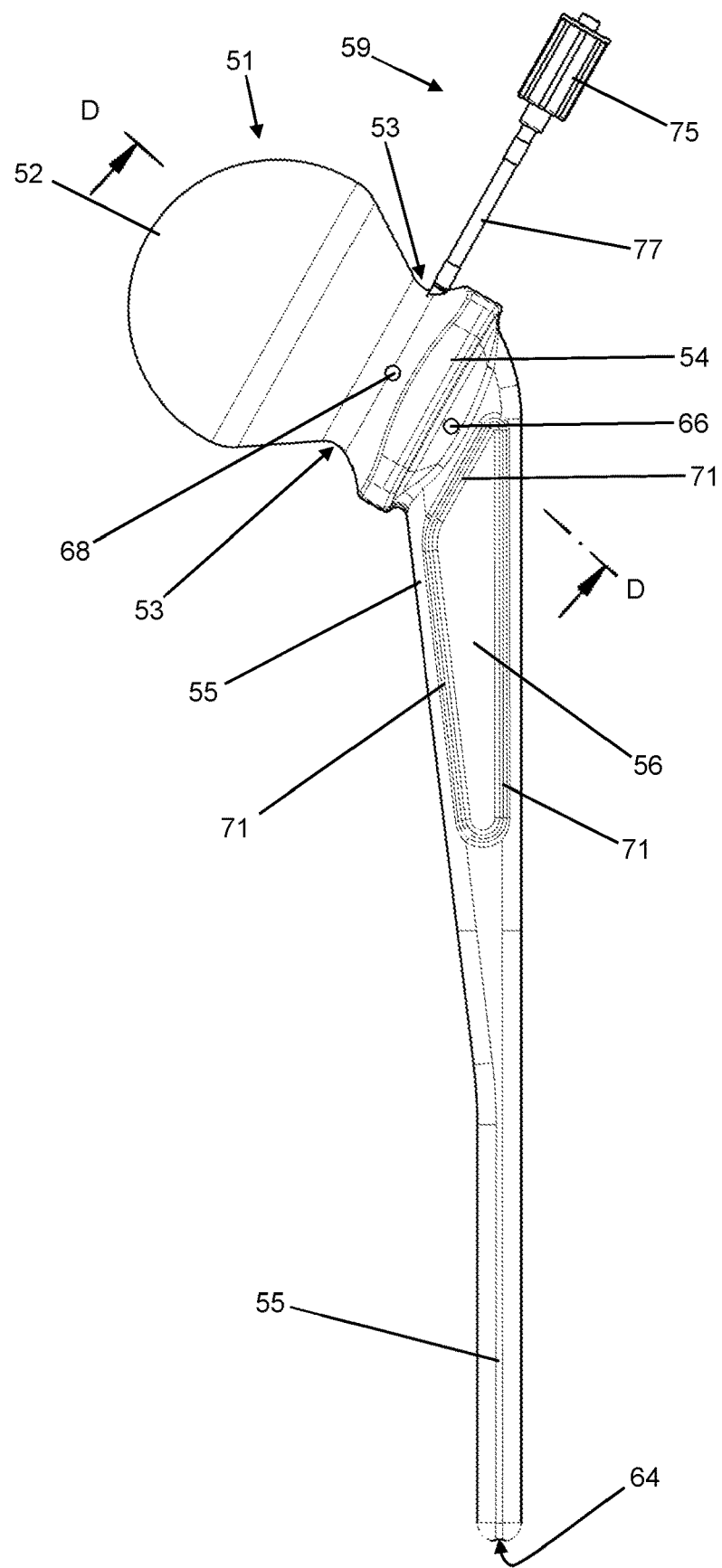
FIG. 11 is a schematic side view of the second hip joint spacer according to the invention illustrated in FIGS. 8 to 10 but onto the opposite side from FIG. 9.
Figure 12:
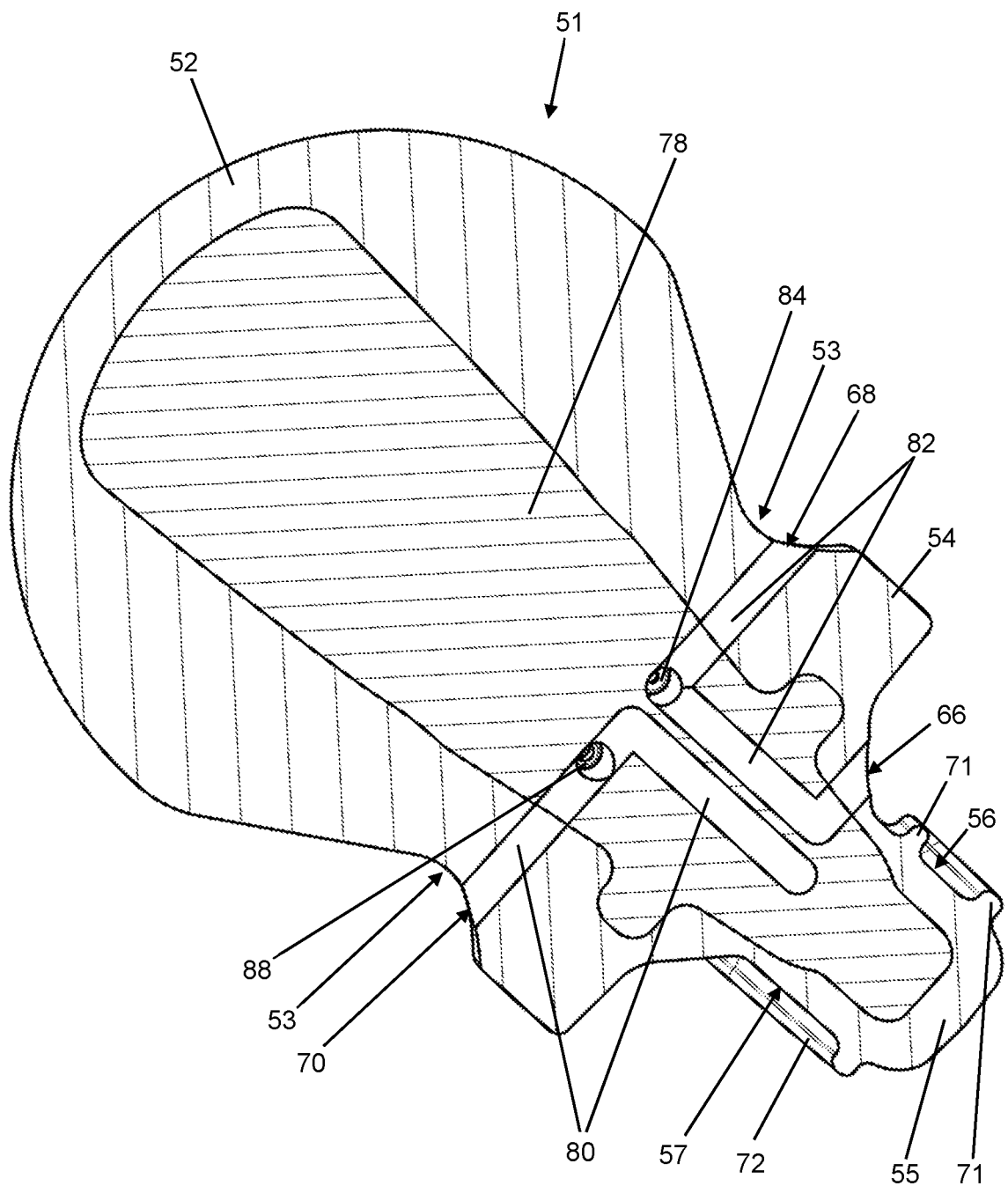
FIG. 12 is a schematic cross-sectional view of the second hip joint spacer according to the invention corresponding to section D in FIG. 11, wherein the section plane extends perpendicular to the section plane of FIG. 10.
Figure 13:
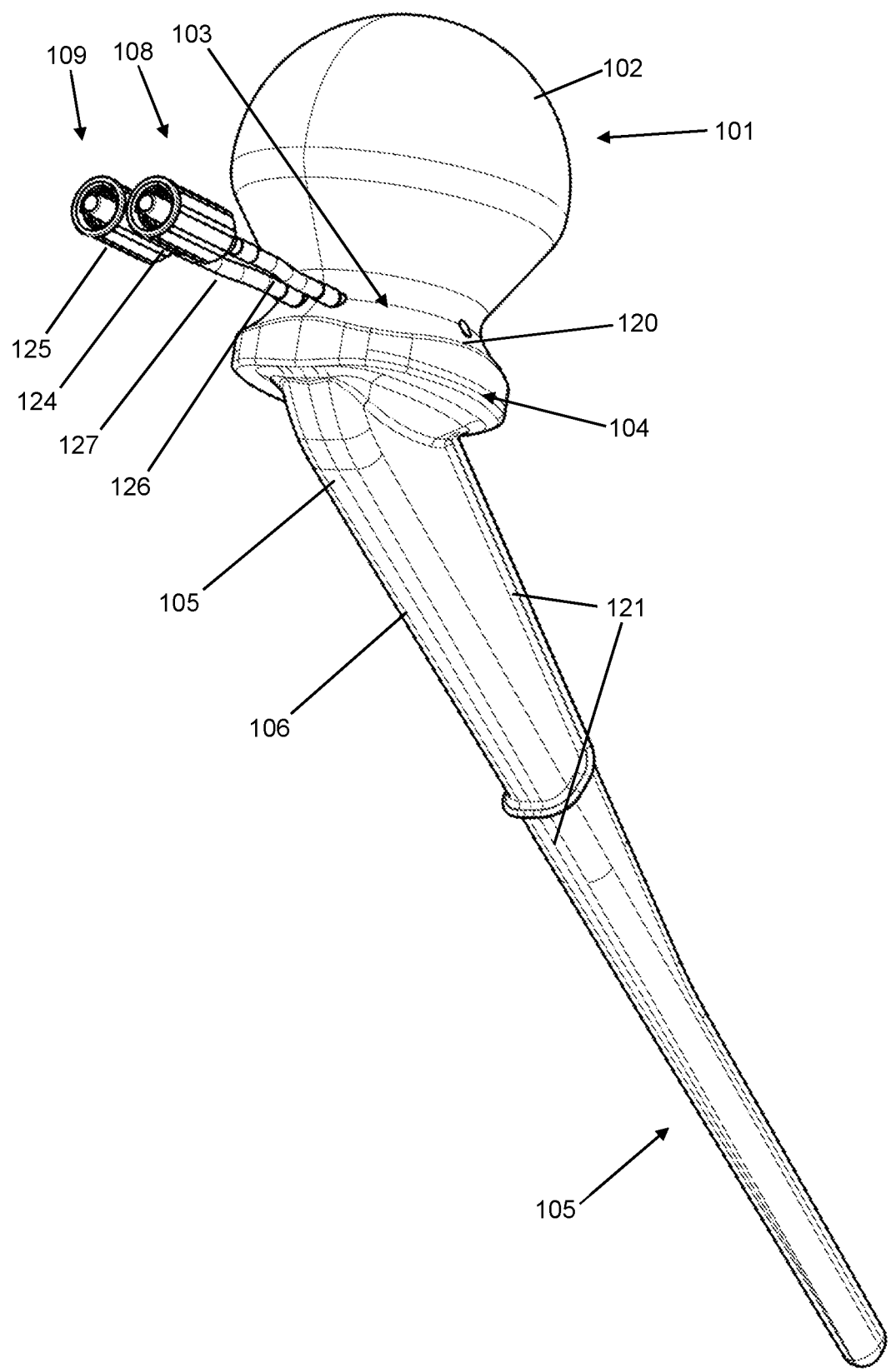
FIG. 13 is a schematic perspective external view of a third hip joint spacer according to the invention with an irrigation device.
Figure 14:
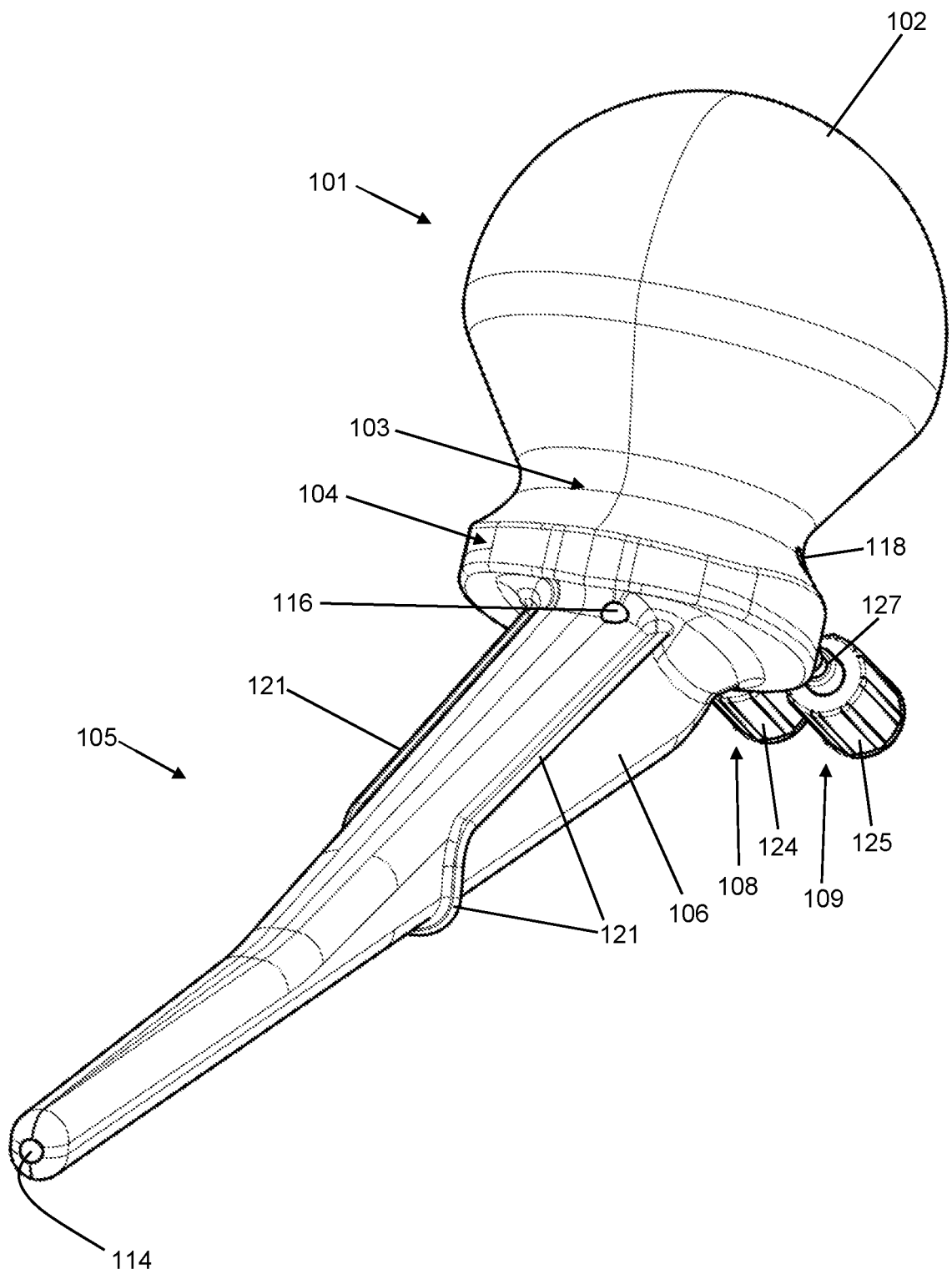
FIG. 14 is a schematic perspective external view of the third hip joint spacer according to the invention illustrated in FIG. 13 but onto the opposite side.

In the cross-sectional views according to FIGS. 10 and 12, it is apparent how the irrigation liquid outlet opening 69 is connected to the first irrigation liquid intake opening 66 and to the second irrigation liquid intake opening 68 and the irrigation liquid inlet opening 67 is connected to the first irrigation liquid discharge opening 64 and to the second irrigation liquid discharge opening 70 inside the prosthesis body. In the case of a section similar to section A in FIG. 3a cross-section similar to FIG. 4 would result for the second exemplary hip joint spacer. The cross-sectional views also show that the hip joint spacer has a core 78 of a metal, while the outer regions of the prosthesis body are made substantially of a plastic material, preferably of a bone cement, such as a PMMA plastic, which may be loaded with an antibiotic or with a plurality of antibiotics.

Inside the prosthesis body the irrigation liquid inlet opening 67 is connected to the first irrigation liquid, discharge opening 64 and the second irrigation liquid discharge opening 70 via a first duct 80. The duct 80 produces a liquid-conveying connection between the irrigation liquid inlet opening 67 and the first irrigation liquid discharge opening 64 and the second irrigation liquid discharge opening 70. To this end, inside the prosthesis body, in the region of the cross-section at the neck 53, a branch in the form of a T-piece is present in the first duct 80. Likewise, inside the prosthesis body the irrigation liquid outlet opening 69 is connected to the first irrigation liquid intake opening 66 and the second irrigation liquid intake opening 68 via a second duct 82. For this purpose, the second duct 82 also comprises a branch. The first duct 80 and the second duct 82 are separated from one another inside the prosthesis body.

A valve element 84 is provided in the second duct 82, directly in front of the irrigation liquid outlet opening 69, the valve element 84 allowing outflow of liquid from the second duct 82 through the irrigation liquid outlet opening 69 out of the prosthesis body into the second connector 59 and preventing backflow from the second connector 59 into the second duct 82. The second connector 59 is connected to the irrigation liquid outlet opening 69 via a detachable connecting element 86.

A valve element 88 is provided in the first duct 80, directly in front of the irrigation liquid inlet opening 67, the valve element 88 allowing inflow of the medical irrigation liquid into the first duct 80 through the irrigation liquid inlet opening 67 into the prosthesis body and preventing backflow from the first duct 80 into the first connector 58. The first connector 58 is connected to the irrigation liquid inlet opening 67 via a detachable connecting element 90.

The first connector 58 and the second connector 59 may be detached from the prosthesis body by pulling or screwing off the detachable connecting elements 86, 90. To this end, liquid-conveying mating fastening elements 92, 94 are provided in the ducts 80, 82 in the prosthesis body. The mating fastening elements 92, 94 may for example be made from sleeves with internal threads, into which the connecting elements 86, 90 in the form of liquid-conveying sleeves with external threads have been or can be screwed.

In the inserted state, the femoral hip joint spacer may be used as follows for irrigation. A medical irrigation liquid with a composition adapted to the patient's needs, such as for example a sterile Ringer's solution with a mixture of suitable antibiotics, is fed through the first connector 58 into the prosthesis body. The medical irrigation liquid flows through the valve element 88 and through the first duct 80 through the prosthesis body and exits through the first irrigation liquid discharge opening 64 and through the second irrigation liquid discharge opening 70 out of the prosthesis body. The irrigation liquid then flows along the surface of the hip joint spacer from the first irrigation liquid discharge opening 64 to the first irrigation liquid intake opening 66 and from the second irrigation liquid discharge opening 70 to the second irrigation liquid intake opening 68. In the process, the irrigation liquid flows around the fastening area 56 separated by the rib 71. The regions therebetween are irrigated with a film of the medical irrigation liquid. The used irrigation liquid re-enters the prosthesis body at the first irrigation liquid intake opening 66 and the second irrigation liquid intake opening 68 and flows through the second duct 82 and the valve element 88 to the irrigation liquid outlet opening 69. Front there the used irrigation liquid is removed by suction from the prosthesis body through the second connector 59 and the used irrigation liquid is disposed of or collected.

If no further irrigation is to take place, the connectors 58, 59 with the connecting elements 86, 90 are separated from the prosthesis body and the remaining hip joint spacer may also he used like a normal hip joint spacer. Provision may preferably be made for the irrigation liquid inlet opening 67 and the irrigation liquid outlet opening 69 to close automatically on pulling or screwing the connecting elements 86, 90 off the prosthesis body.

As a variant of the second exemplary hip joint spacer, the distal irrigation liquid intake opening 66 and the proximal irrigation liquid discharge opening 70 could be closed. A single circuit of the irrigation liquid would thereby be produced via the distal irrigation liquid discharge opening 64 and the proximal irrigation liquid intake opening 68, the circuit extending both over the distal and over the proximal side of the hip joint spacer. The irrigation liquid has then to flow over the collar 54.

FIGS. 13 to 18 show depictions of a third exemplary embodiment of a hip joint spacer according to the invention with an irrigation device. The femoral hip joint spacer has a ball head 101 with a sliding surface 102 on the proximal side. The sliding surface 102 rests when inserted against the hip joint socket and thereby forms a part of the hip joint. On the distal side opposite the sliding surface 102, the ball head 101 is connected to a collar 104 via a neck 103. The neck 103 is thinner than the ball head 101 and the collar 104. On the distal side of the collar 104 a stem 105 is attached, which extends in the distal direction and serves in fastening the hip joint spacer in the femur. To this end, the hip joint spacer has a fastening area 106 which extends over a plurality of sides of the stem 105 and is provided to connect the hip joint spacer to the femur with the aid of bone cement paste. The ball head 101, the neck 103, the collar 104 and the stem 105 form a prosthesis body of the hip joint spacer. The prosthesis body corresponds in this respect in its external shape to the first exemplary hip joint spacer illustrated in FIGS. 1 to 7 and the second exemplary hip joint spacer illustrated in FIGS. 8 to 12, apart from the shape of the fastening area 106 and the fact that only one fastening area 106 is present.

Unlike with known hip joint spacers, on one side of the third exemplary hip joint spacer a first tubular connector 108 is fastened to an irrigation liquid inlet opening and a second tubular connector 109 is fastened to an irrigation liquid outlet opening. The irrigation liquid inlet opening and the irrigation liquid outlet opening lead into the inside of the prosthesis body and are arranged in the region of the neck 103. The first tubular connector 108 and the second tubular connector 109 are liquid-conveying, such that a medical irrigation liquid can be passed through the first tubular connector 108 into the prosthesis body and a liquid can be drained out of the prosthesis body through the second tubular connector 109. The first connector 108 and the second connector 109 are connected detachably to the irrigation liquid inlet opening and the irrigation liquid outlet opening.

At the distal end of the stem 105 a first irrigation liquid discharge opening 114 is arranged and at the point of transition from the stem 105 to the collar 104 a first irrigation liquid intake opening 116 is arranged. Furthermore, a second irrigation liquid intake opening 118 is arranged on the neck 103 or at the point of transition from the neck 103 to the collar 104 and a second irrigation liquid discharge opening 120 is arranged on the opposite side from the second irrigation liquid intake opening 118 on the neck 103 or at the point of transition from the neck 103 to the collar 104. The first irrigation liquid discharge opening 114 and the first irrigation liquid intake opening 116 are thereby arranged on the distal side of the hip joint spacer and the second irrigation liquid discharge opening 120 and the second irrigation liquid intake opening 118 are arranged on the proximal side of the hip joint spacer, wherein the proximal and distal sides are separated by the collar 104. The first irrigation liquid discharge opening 114 and the first irrigation liquid intake opening 116 on the one hand and the second irrigation liquid discharge opening 120 and the second irrigation liquid intake opening 118 on the other hand are thereby suited to forming two medical irrigation liquid circuits, separated by the collar 104, along the distal and proximal surfaces of the hip joint spacer.

The fastening area 106 is delimited by a peripheral rib 121 and on the proximal side of the fastening area 106 by the collar 104. The rib 121 extends up out of the surface of the stem 105 and reaches on two opposing sides of the stem 105 as far as the collar 104. The rib 121 should be understood as being part of the prosthesis body. The purpose of the projecting rib 121 and the collar 104 is to prevent bone cement paste from reaching, or at least hinder the paste from reaching, outside the fastening area 106 on fastening of the hip joint spacer to the femur and thereby closing or impeding the first irrigation liquid discharge opening 114, the first irrigation liquid intake opening 116, the second irrigation liquid discharge opening 120, the second irrigation liquid intake opening 118 or the irrigation liquid inlet opening and the irrigation liquid outlet opening or undesirably cementing firm the first connector 108 or the second connector 109 on the prosthesis body.

The first connector 108 has a Luer Lock adapter 124 and a short, flexible hose 126. The second connector 109 likewise has a Luer Lock adapter 125 and a short, flexible hose 127. In this way, the hip joint spacer may be connected by the first connector 108 via the Luer Lock adapter 124 to a source of a medical irrigation liquid with a pump (not shown) and the second connector 109 via the Luer Lock adapter 126 to a collecting vessel and optionally likewise a pump (not shown).

Figure 15:
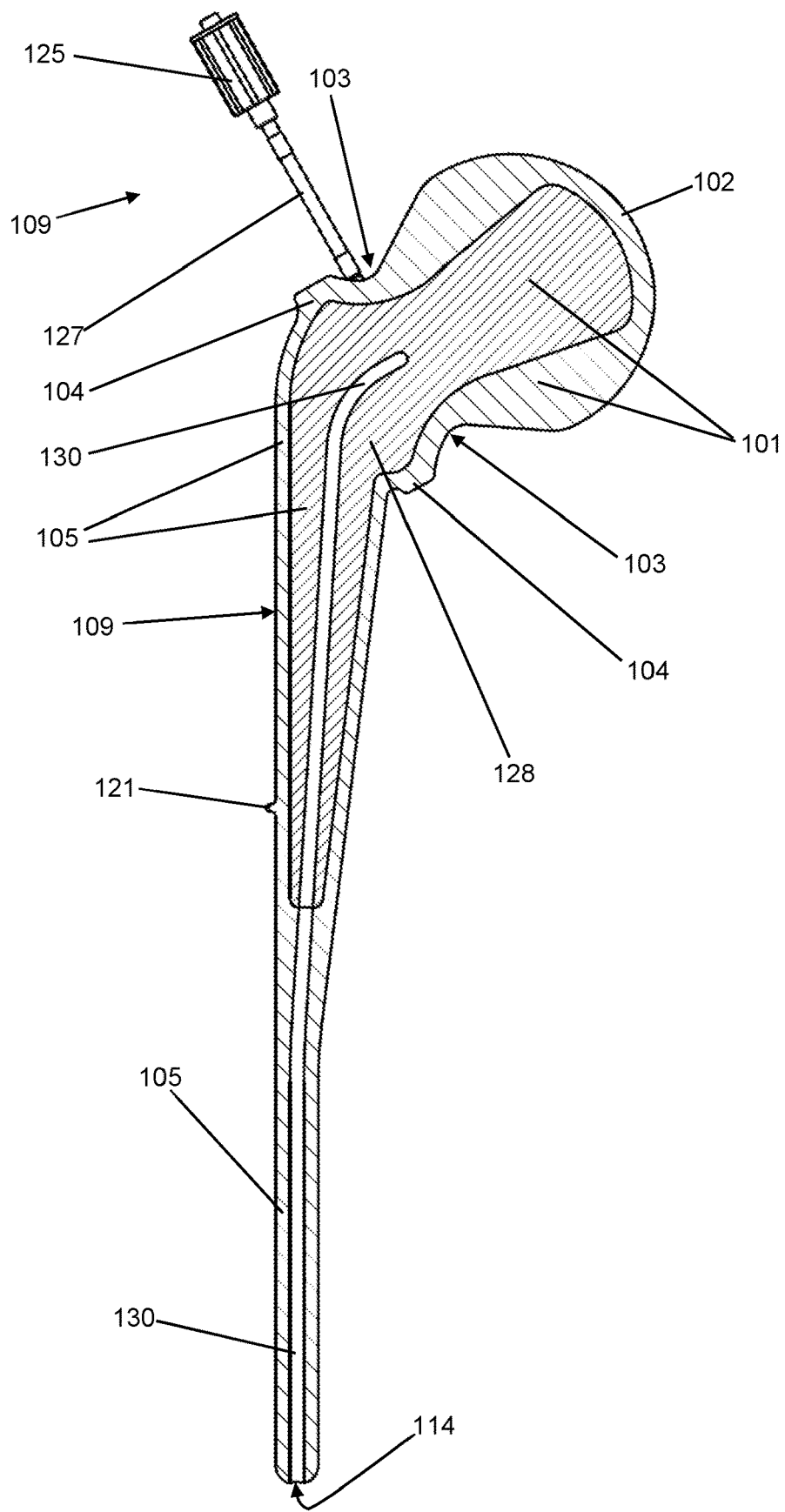
FIG. 15 is a schematic cross-sectional view of the third hip joint spacer according to the invention illustrated in FIGS. 13 and 14, wherein the section extends in the front plane.
Figure 16:
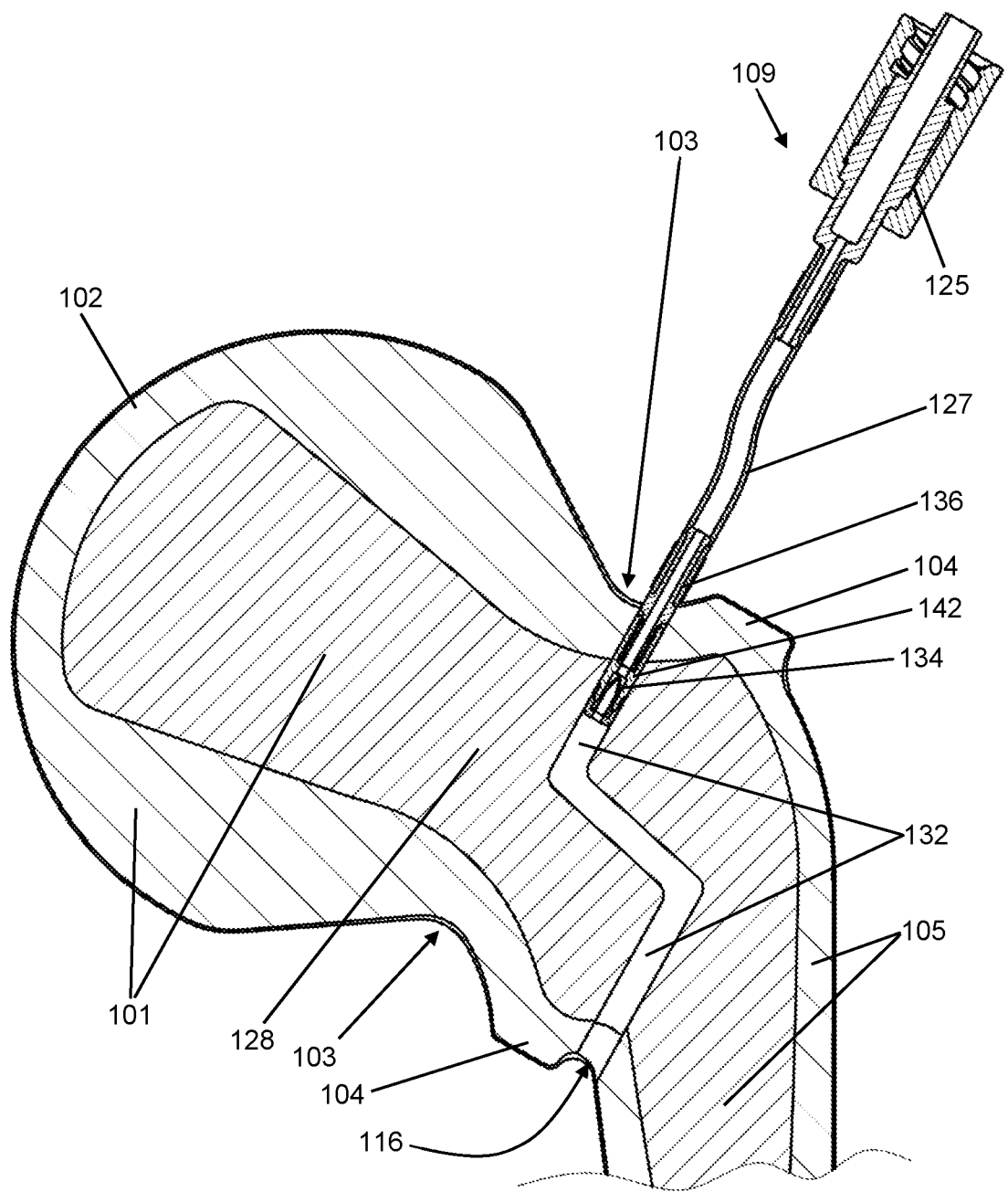
FIG. 16 is a schematic cross-sectional view through a portion of the third hip joint spacer according to the invention, wherein the section plane extends parallel to that according to FIG. 15.
Figure 17:
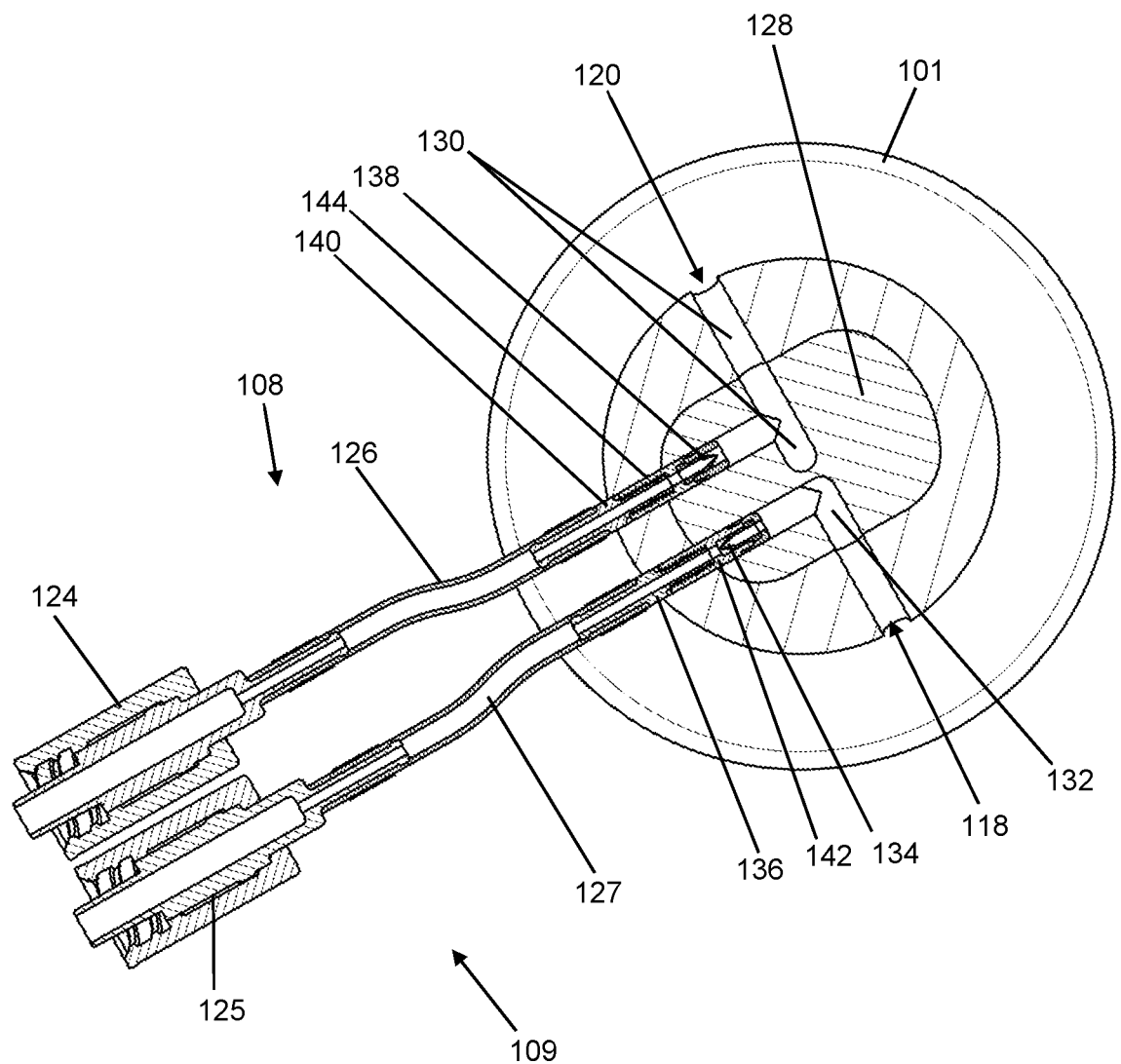
FIG. 17 is a schematic cross-sectional view of the third hip joint spacer according to the invention illustrated in FIGS. 13 to 16, wherein the section plane extends perpendicular to the section plane of FIGS. 15 and 16.
Figure 18:
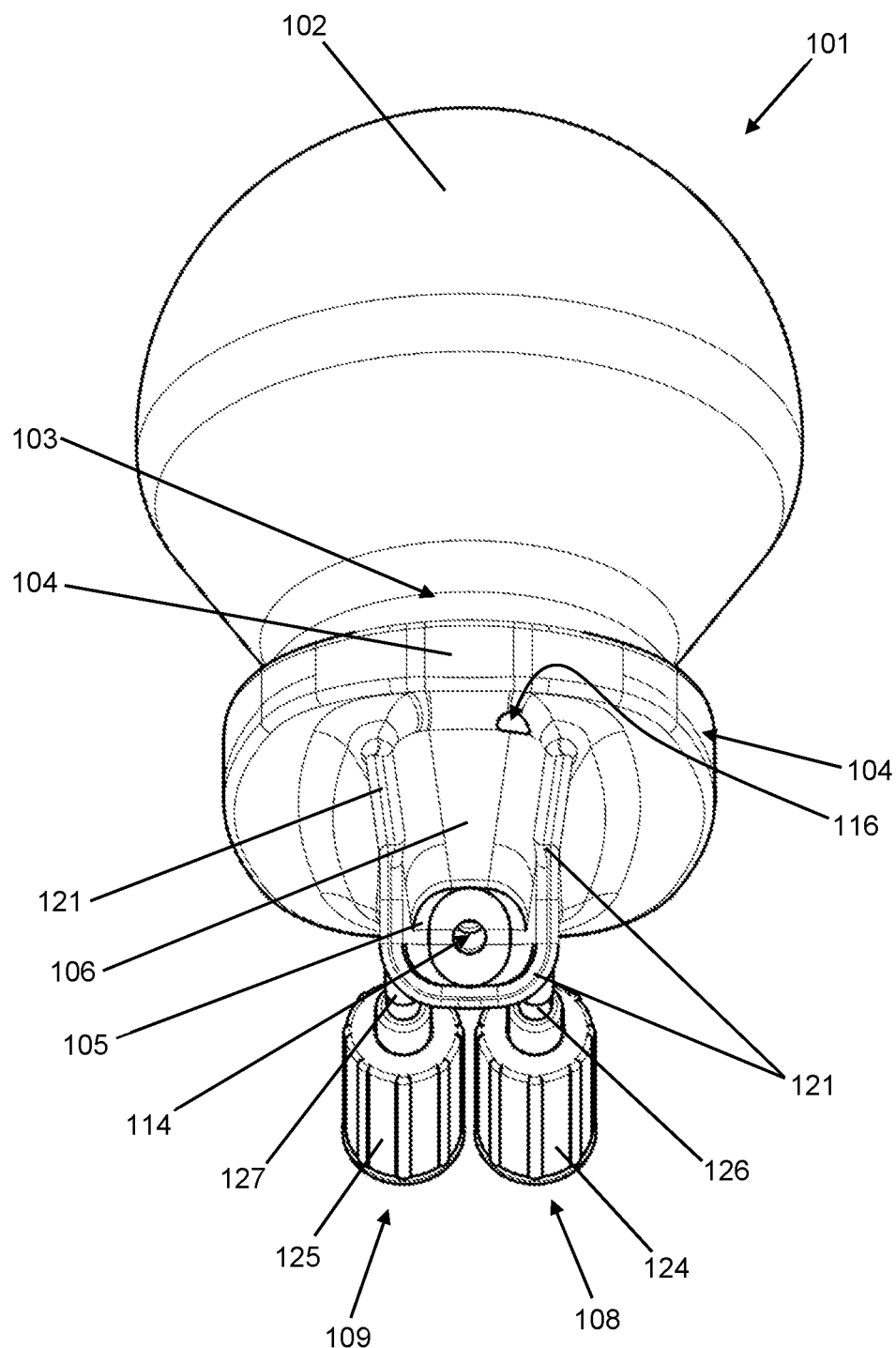
FIG. 18 is a further schematic perspective external view of the third hip joint spacer according to the invention illustrated in FIGS. 13 to 17 but onto the distal end of the stem.

In the cross-sectional views according to FIGS. 15, 16 and 17, it is apparent how the irrigation liquid outlet opening is connected to the first irrigation liquid intake opening 116 and to the second irrigation liquid intake opening 118 and the irrigation liquid inlet opening is connected to the first irrigation liquid discharge opening 114 and to the second irrigation liquid discharge opening 120 inside the prosthesis body. The cross-sectional views further show that the hip joint spacer has a core 128 of a metal, while the outer regions of the prosthesis body are made substantially of a plastic material, preferably of a bone cement, such as a PMMA plastic, which may be loaded with an antibiotic or with a plurality of antibiotics.

Inside the prosthesis body the irrigation liquid inlet opening is connected to the first irrigation liquid discharge opening 114 and the second irrigation liquid discharge opening 120 via a first duct 130. The duct 130 produces a liquid-conveying connection between the irrigation liquid inlet opening and the first irrigation liquid discharge opening 114 and the second irrigation liquid discharge opening 120. To this end, inside the prosthesis body, in the region of the cross-section at the neck 103, a branch in the form of a T-piece is present in the first duct 130. Likewise, inside the prosthesis body the irrigation liquid outlet opening is connected to the first irrigation liquid intake opening 116 and the second irrigation liquid intake opening 118 via a second duct 132. For this purpose, the second duct 132 also comprises a branch. The first duct 130 and the second duct 132 are separated from one another inside the prosthesis body.

A valve element 134 is provided in the second duct 132, directly in front of the irrigation liquid outlet opening, the valve element 134 allowing outflow of liquid from the second duct 132 through the irrigation liquid outlet opening out of the prosthesis body into the second connector 109 and preventing backflow from the second connector 109 into the second duct 132. The second connector 109 is connected to the irrigation liquid outlet opening via a detachable connecting element 136.

A valve element 138 is provided in the first duct 130, directly in front of the irrigation liquid inlet opening, the valve element 138 allowing inflow of the medical irrigation liquid into the first duct 130 through the irrigation liquid inlet opening into the prosthesis body and preventing backflow from the first duct 130 into the first connector 108. The first connector 108 is connected to the irrigation liquid inlet opening via a detachable connecting element 140.

The first connector 108 and the second connector 109 may be detached from the prosthesis body by pulling or screwing off the detachable connecting elements 136, 140. To this end, liquid-conveying mating fastening elements 142, 144 are provided in the ducts 130, 132 in the prosthesis body. The mating fastening elements 142, 144 may for example be made from sleeves with internal threads, into which the connecting elements 136, 140 in the form of liquid-conveying sleeves with external threads have been or can be screwed.

In the inserted state, the femoral hip joint spacer may be used as follows for irrigation. A medical irrigation liquid with a composition adapted to the patient's needs, such as for example a sterile Ringer's solution with a mixture of suitable antibiotics, is fed through the first connector 108 into the prosthesis body. The medical irrigation liquid flows through the valve element 138 and through the first duct 130 through the prosthesis body and exits through the first irrigation liquid discharge opening 114 and through the second irrigation liquid discharge opening 120 out of the prosthesis body. The irrigation liquid then flows along the surface of the hip joint spacer from the first irrigation liquid discharge opening 114 to the first irrigation liquid intake opening 116 and from the second irrigation liquid discharge opening 120 to the second irrigation liquid intake opening 118. The regions therebetween are irrigated with a film of the medical irrigation liquid. The used irrigation liquid re-enters the prosthesis body at the first irrigation liquid intake opening 116 and the second irrigation liquid intake opening 118 and flows through the second duct 132 and the valve element 138 to the irrigation liquid outlet opening. From there the used irrigation liquid is removed by suction from the prosthesis body through the second connector 109 and the used irrigation liquid is disposed of or collected.

If no further irrigation is to take place, the connectors 108, 109 with the connecting elements 136, 140 are separated from the prosthesis body and the remaining hip joint spacer may also be used like a normal hip joint spacer. Provision may preferably be made for the irrigation liquid inlet opening and the irrigation liquid outlet opening to close automatically on pulling or screwing the connecting elements 136, 140 off the prosthesis body.

As a variant of the third exemplary hip joint spacer, the distal irrigation liquid intake opening 116 and the proximal irrigation liquid discharge opening 120 could be closed. A single circuit of the irrigation liquid would thereby be produced via the distal irrigation liquid discharge opening 114 and the proximal irrigation liquid intake opening 118, the circuit extending both over the distal and over the proximal side of the hip joint spacer. The irrigation liquid has then to flow over the collar 104.

Figure 19:
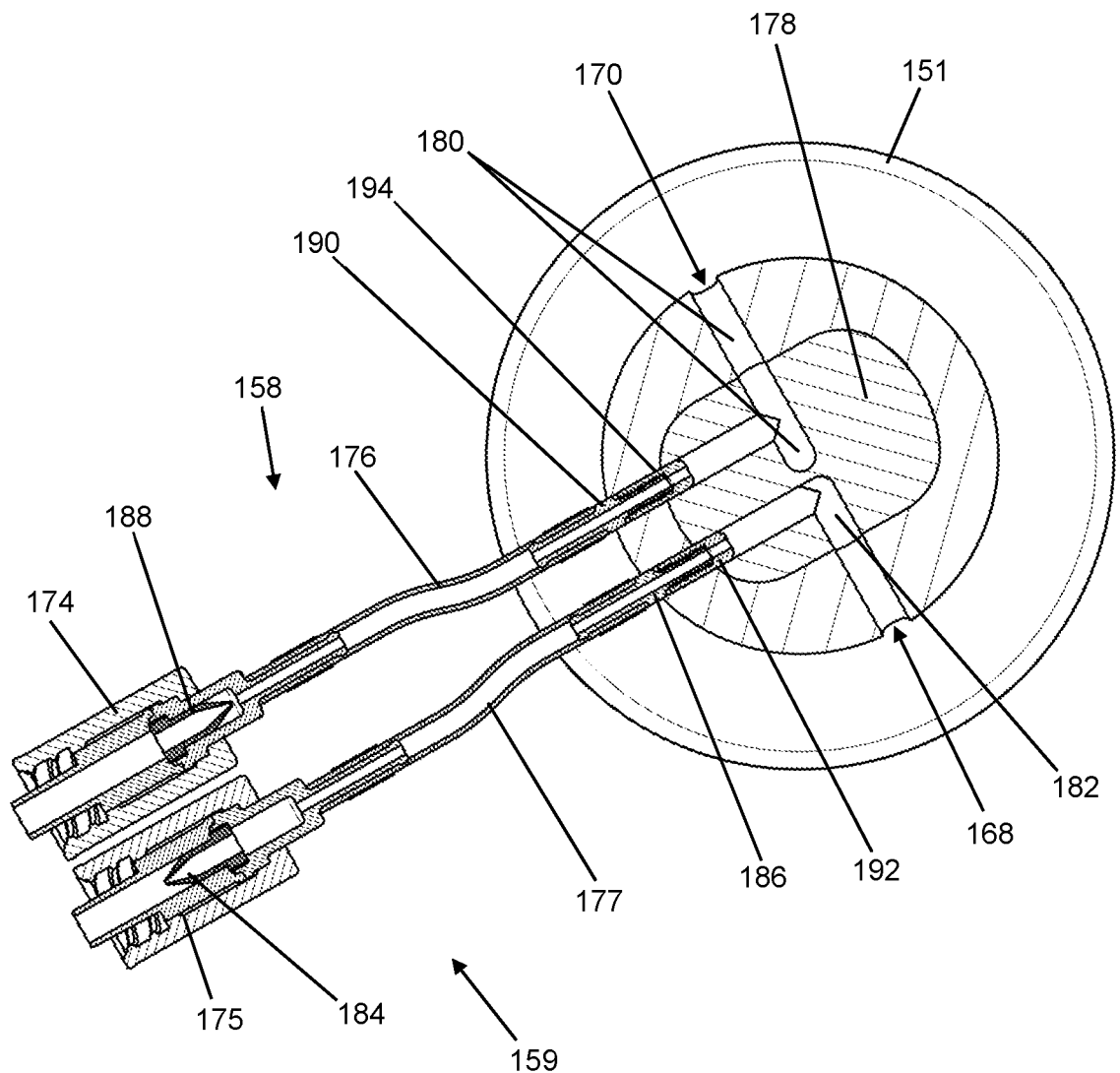
FIG. 19 is a schematic cross-sectional view through a variant of the first, second and third hip joint spacer according to the invention which is constructed just like the first, second or third hip joint spacer according to the invention apart from the arrangement of valve elements.

FIG. 19 shows a schematic cross-sectional view through a variant of the first, second, third and a subsequent fourth hip joint spacer according to the invention which is constructed just like the first, second, third or fourth hip joint spacer according to the invention apart from the arrangement of the valve elements 184, 188. The valve elements 184, 188 are namely not arranged inside the prosthesis body, but rather in two connectors 158, 159 or more precisely in Luer Lock adapters 174, 175 of the connectors 158, 159. The valve elements 184, 188 are then removed when required together with the connecting elements 186, 190 and the hoses 176, 177 of the connectors 158, 159. To do this, the connectors 158, 159 may be screwed out of matching mating fastening elements 192, 194 or separated from the prosthesis body in some other way.

Since the variant shown in FIG. 19 may otherwise be selected to be identical to the first, second, third and the subsequent fourth embodiment apart from the arrangement of the valve elements 184, 188, in these variants the hip joint spacer has a core 178 of metal, a ball head 151 and ducts 180, 182 inside the prosthesis body. Furthermore, FIG. 19 shows the second irrigation liquid intake opening 168 and the second irrigation liquid discharge opening 170.

Figure 20:
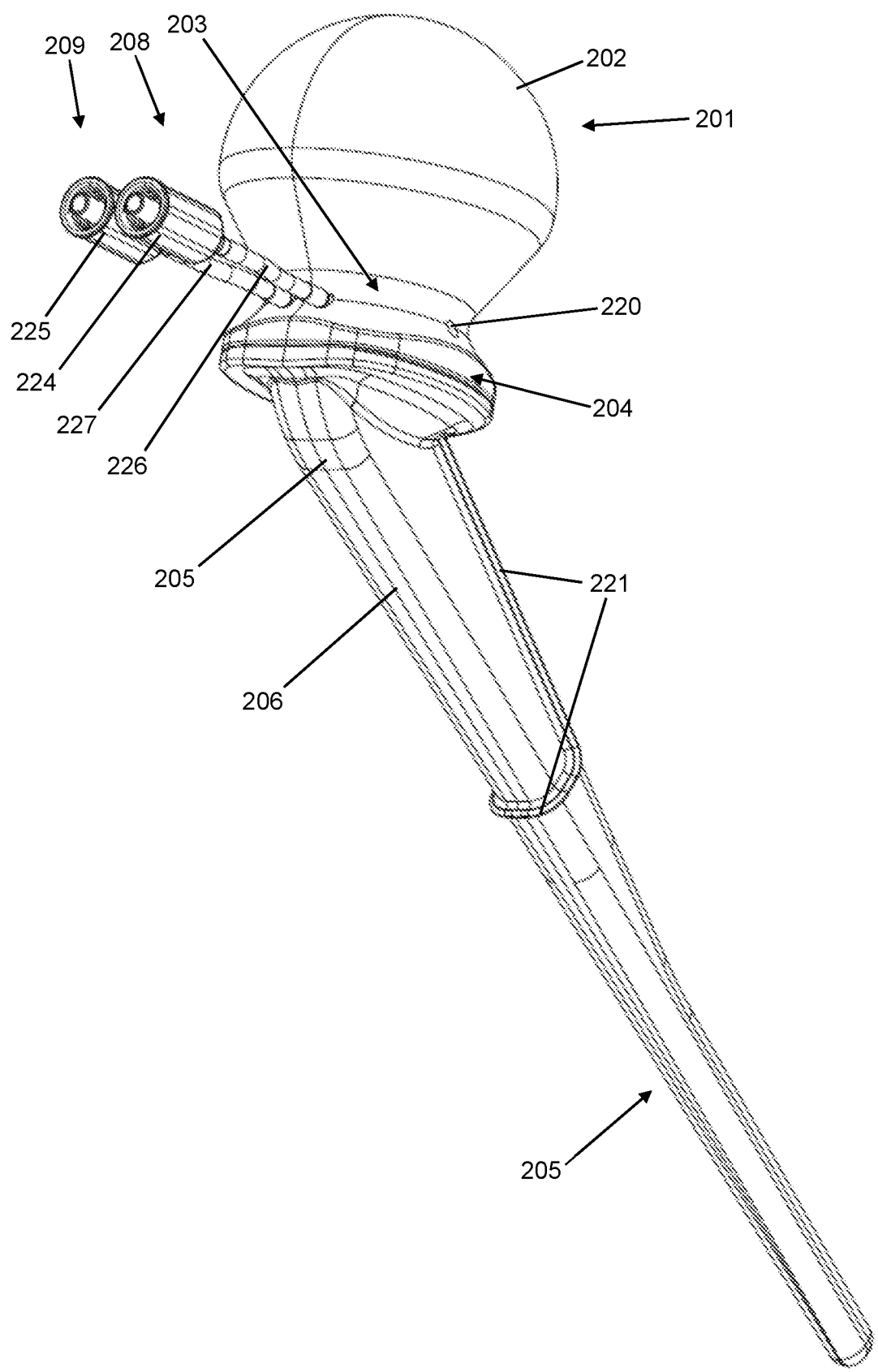
FIG. 20 is a schematic perspective external view of a fourth, multipart hip joint spacer according to the invention with an irrigation device.
Figure 21:
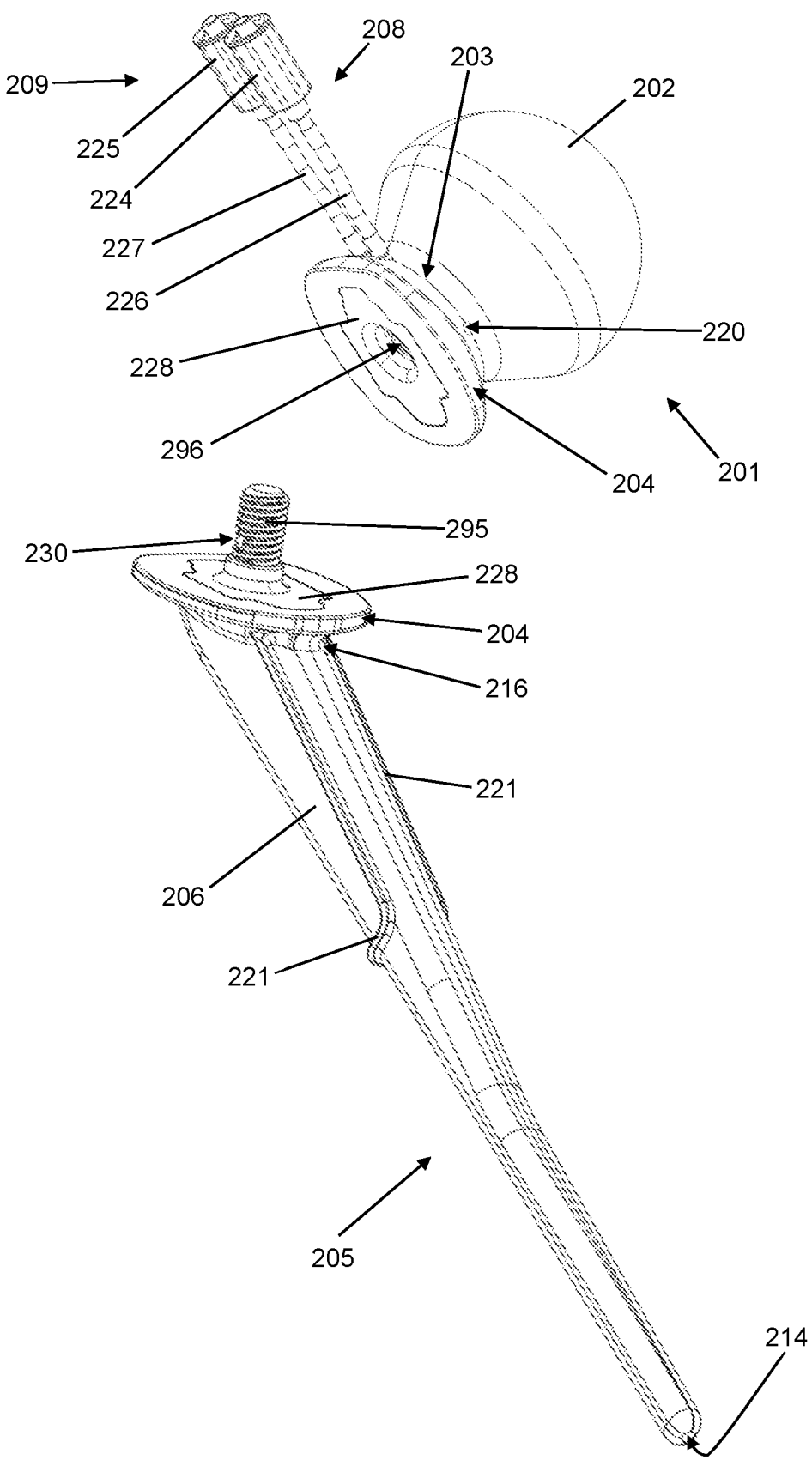
FIG. 21 is a further schematic perspective external view of the fourth, multipart hip joint spacer according to the invention illustrated in FIG. 20 in the exploded state.
Figure 22:
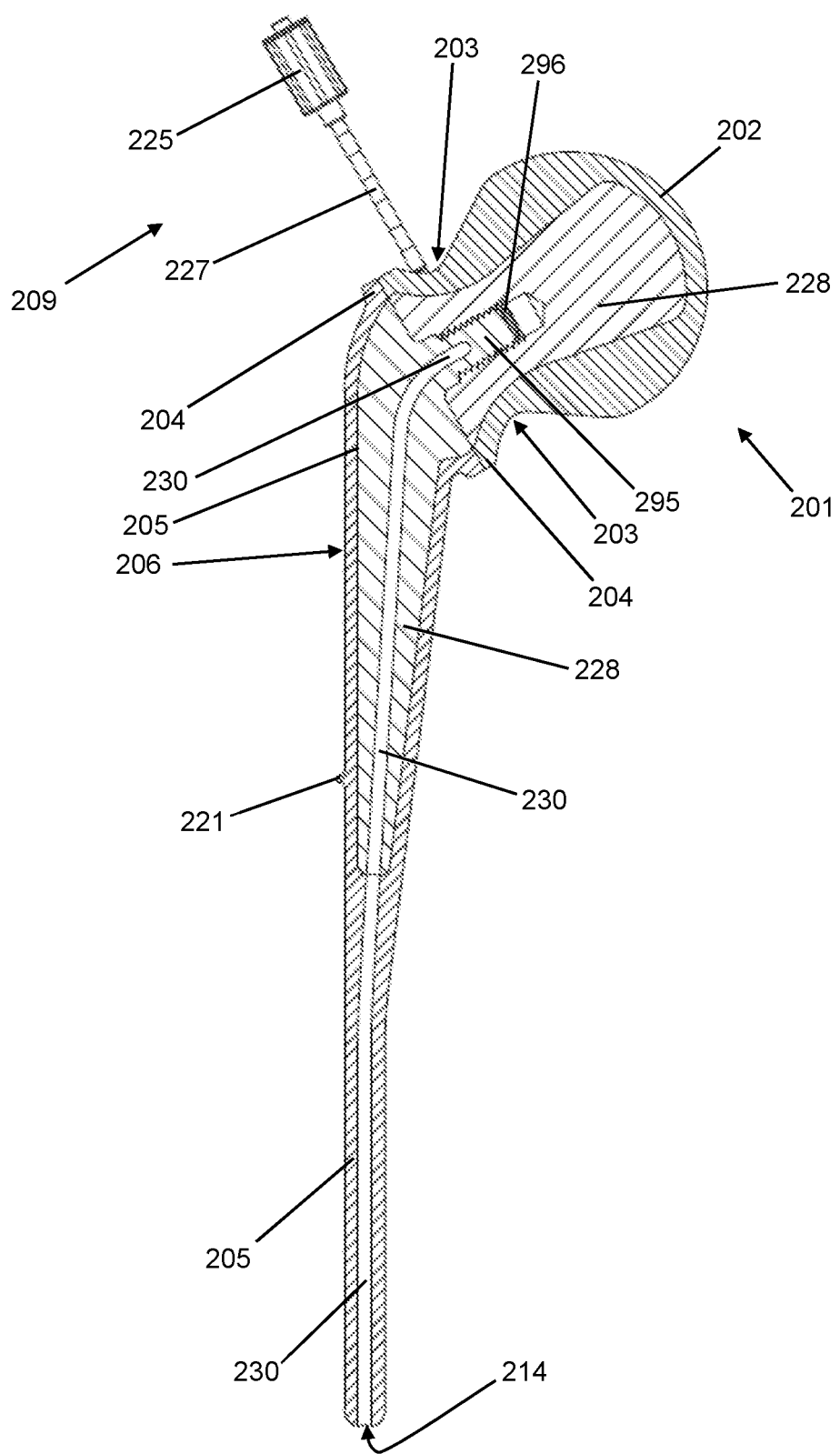
FIG. 22 is a schematic cross-sectional view through the fourth hip joint spacer according to the invention illustrated in FIGS. 20 and 21.

FIGS. 20 to 22 show depictions of a fourth, multipart exemplary embodiment of a hip joint spacer according to the invention with an irrigation device, which corresponds to the third exemplary embodiment illustrated in FIGS. 13 to 18 apart from the divisibility. To avoid repetition, for details reference is thus made to the third exemplary embodiment. The femoral hip joint spacer accordingly has a ball head 201 with a sliding surface 202 on the proximal side. On the distal side opposite the sliding surface 202, the ball head 201 is connected to a collar 204 via a neck 203. A stem 205 extending in the distal direction is attached to the distal side of the collar 204. To this end, the hip joint spacer has a fastening area 206 which extends over a plurality of sides of the stem 205 and is provided to connect the hip joint spacer to the femur with the aid of bone cement paste. The ball head 201, the neck 203, the collar 204 and the stem 205 form a prosthesis body of the hip joint spacer, wherein the prosthesis body is separable in the middle of the collar 204 in that the head part (at the top in FIGS. 20 to 22) can be unscrewed from the stem part (at the bottom in FIGS. 20 to 22). In this way, different head parts (not shown) may be screwed on to fit the anatomy of the patient. The various head parts differ in this respect in different diameters of the ball head 201, such that the hip joint spacer may be adapted to hip joint sockets of different sizes.

On one side of the fourth exemplary hip joint spacer, a first tubular connector 208 is detachably fastened in a liquid-conveying manner to an irrigation liquid inlet opening and a second tubular connector 209 is detachably fastened in a liquid-conveying manner to an irrigation liquid outlet opening. The irrigation liquid inlet opening and the irrigation liquid outlet opening lead into the inside of the prosthesis body and are arranged in the region of the neck 203.

At the distal end of the stem 205 a first irrigation liquid discharge opening 214 is arranged and at the point of transition from the stem 205 to the collar 204 a first irrigation liquid intake opening 216 is arranged. Furthermore, a second irrigation liquid discharge opening 220 is arranged on the neck 203 or at the point of transition from the neck 203 to the collar 204 and a second irrigation liquid intake opening (not visible) is arranged on the neck 203 on the opposite side from the second irrigation liquid discharge opening 220. The first irrigation liquid discharge opening 214 and the first irrigation liquid intake opening 216 are thereby arranged on the distal stem part of the hip joint spacer and the second irrigation liquid discharge opening 220 and the second irrigation liquid intake opening are arranged on the proximal head part of the two-part hip joint spacer. The first irrigation liquid discharge opening 214 and the first irrigation liquid intake opening 216 on the one hand and the second irrigation liquid discharge opening 220 and the second irrigation liquid intake opening on the other hand are suited to forming two medical irrigation liquid circuits, separated by the collar 204, along the distal and proximal surfaces of the hip joint spacer.

The fastening area 206 is delimited by a peripheral rib 221 and on the proximal side of the fastening area 206 by the collar 204. The rib 221 extends up out of the surface of the stem 205 and reaches on two opposing sides of the stem 205 as far as the collar 204, and should be understood as being part of the prosthesis body.

The first connector 208 has a Luer Lock adapter 224 and a short, flexible hose 226. The second connector 209 likewise has a Luer Lock adapter 225 and a short, flexible hose 227.

In the cross-sectional view according to FIG. 22, it is indicated that the irrigation liquid outlet opening is connected to the first irrigation liquid intake opening 216 and to the second irrigation liquid intake opening and the irrigation liquid inlet opening is connected to the first irrigation liquid discharge opening 214 and to the second irrigation liquid discharge opening 220 inside the prosthesis body, as in the third exemplary embodiment. In addition, it is clear from the cross-sectional view according to FIG. 20 and apparent in the exploded representation in FIG. 21 that the hip joint spacer has a core 228 of a metal, while the external regions of the prosthesis body are made substantially from a plastic material which may be mixed with a pharmaceutically active substance.

Inside the prosthesis body the irrigation liquid inlet opening is connected to the first irrigation liquid discharge opening 214 and the second irrigation liquid discharge opening 220 via a first duct 230. The duct 230 produces a liquid-conveying connection between the irrigation liquid inlet opening and the first irrigation liquid discharge opening 214 and the second irrigation liquid discharge opening 220. Likewise, inside the prosthesis body the irrigation liquid outlet opening is connected to the first irrigation liquid intake opening 216 and the second irrigation liquid intake opening via a second duct (not visible). The first duct 230 and the second duct are separated from one another inside the prosthesis body.

The stem part and the various head parts may be screwed together via a threaded rod 295 with an external thread on the stem part and via a threaded bore 296 with a matching internal thread in the head part. The duct 230 is in this case guided by the threaded rod 295 and the thread.

It is alternatively also possible for the multipart hip joint spacer to be separated or separable in such a way at the point of transition from the neck 203 to the ball head 201 or on the ball head 201 that the ducts 130 and all the openings 214, 216, 220 and the connectors 208, 209 are arranged on the stem part. In this way the duct 230 does not require any transition at the connection of head part to stem part.

The use of a PMMA mixed with antibiotics or antimycotics or other pharmaceutically active substances at least as an external layer of hip joint spacers according to the invention has the advantage that a particularly large quantity of the active ingredients is available initially over a large area. In addition, a particular combinatorial effect results, namely that circulation of the medical irrigation liquid promotes and enhances release of the active ingredients at the surface of the hip joint spacer.

The features of the invention disclosed in the above description, as well as in the claims, figures and exemplary embodiments, may be essential both individually and in any desired combination to realization of the invention in its various embodiments.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. It is expressly intended, for example, that the steps of the methods of using the various devices disclosed above are not restricted to any particular order.

What is claimed:

1. A femoral hip joint spacer for temporary replacement of a part of a hip joint, the hip joint spacer comprising:
    a prosthesis body having a surface, a ball head with a sliding surface, a neck connected to the ball head, a collar connected on a proximal side of the collar to the neck, and a stem being connected to a distal side of the collar and including at least one fastening area;
    a first tubular and liquid-conveying connector configured to feed a medical irrigation liquid into the prosthesis body;
    a second tubular and liquid-conveying connector configured to drain the irrigation liquid from the prosthesis body;
    an irrigation liquid inlet opening in the surface of the prosthesis body, wherein the first connector is configured to be connected in a liquid-conveying manner to the irrigation liquid nile opening;

an irrigation liquid outlet opening in the surface of the prosthesis body, wherein the second connector is configured to be connected in a liquid-conveying manner to the irrigation liquid outlet opening; and at least one irrigation liquid discharge opening and at least one irrigation liquid intake opening, each of which are arranged in the surface of the prosthesis body outside the at least one fastening area, wherein the at least one first irrigation liquid discharge opening is connected inside the prosthesis body in a liquid-conveying manner to the irrigation liquid inlet opening and the at least one irrigation liquid intake opening is connected inside the prosthesis body in a liquid-conveying manner to the irrigation liquid outlet opening, wherein the at least one irrigation liquid discharge opening is not connected in a liquid-conveying manner to the irrigation liquid outlet opening inside the prosthesis body and at least one irrigation liquid intake opening is not connected in a liquid-conveying manner to the irrigation liquid inlet opening inside the prosthesis body.

2. The hip joint spacer according to claim 1, further comprising a peripheral rib extending from the surface of the prosthesis body and delimiting the at least one fastening area, such that the at least one fastening area is configured to accommodate bone cement paste within the rib.

3. The hip joint spacer according to claim 2, wherein at least one of the at least one fastening area is regionally delimited by a part of the collar.

4. The hip joint spacer according to claim 1, wherein:
at least one first irrigation liquid discharge opening and at least one first irrigation liquid intake opening are arranged in the surface of the prosthesis body on the distal side of the collar or on the stem outside the at least one fastening area, at least one second irrigation liquid discharge opening and at least one second irrigation liquid intake opening are arranged in the surface of the prosthesis body to the side of the collar or on the proximal side of the collar or on the neck or on the ball head, the at least one first irrigation liquid discharge opening and the at least one second irrigation liquid discharge opening are connected inside the prosthesis body in a liquid-conveying manner to the irrigation liquid inlet opening, and the at least one first irrigation liquid intake opening and the at least one second irrigation liquid intake opening are connected inside the prosthesis body in a liquid-conveying manner to the irrigation liquid outlet opening.

5. The hip joint spacer according to claim 4, wherein the at least one first irrigation liquid discharge opening and the at least one first irrigation liquid intake opening are spaced from one another and the at least one second irrigation liquid discharge opening and the at least one second irrigation liquid intake opening are spaced from one another, wherein the spacing distance is at least 5 mm.

6. The hip joint spacer according to claim 4, further comprising a peripheral rib extending from the surface of the prosthesis body and separating the at least one first irrigation liquid discharge opening and the at least one first irrigation liquid intake opening from the at least one fastening area.

7. The hip joint spacer according to claim 4, wherein at least one irrigation liquid discharge opening of the at least one second irrigation liquid discharge opening and at least one irrigation liquid intake opening of the at least one second irrigation liquid intake opening are arranged on the ball head within 5 mm of the sliding surface.

8. The hip joint spacer according to claim 4, wherein at least one of the at least one first irrigation liquid discharge opening is arranged at the end of the stem and at least one of the at least one first irrigation liquid intake opening is arranged on the distal side of the collar, at the point of transition from the collar to the stem or on the proximal side of the stem.

9. The hip joint spacer according to claim 1, wherein the at least one irrigation liquid discharge opening and the at least one irrigation liquid intake opening are spaced from one another by a distance of at least 5 mm.

10. The hip joint spacer according to claim 1, farther comprising a first adapter engaging the first connector on the side remote from the connection with the irrigation liquid inlet opening and a second adapter engaging the second connector on the side remote from the connection with the irrigation liquid outlet opening.

11. The hip joint spacer, according to claim 1, further comprising:
a first self-sealing coupling arranged at the irrigation liquid inlet opening inside the prosthesis body or at the surface of the prosthesis body, the first self-sealing coupling detachably connecting the first connector to the irrigation liquid inlet opening; and a second self-sealing coupling arranged at the irrigation liquid outlet opening inside the prosthesis body or at the surface of the prosthesis body, the second self-sealing coupling detachably connecting the second connector to the irrigation liquid outlet opening.

12. The hip joint spacer according to claim 1, further comprising a plurality of self-sealing couplings and wherein the irrigation liquid inlet opening is a first irrigation liquid inlet opening and the irrigation liquid outlet opening is a first irrigation liquid outlet opening, wherein a second irrigation liquid inlet opening and a second irrigation liquid outlet opening are additionally provided in the surface of the prosthesis body, wherein one of the plurality of self-sealing couplings is in each case arranged at the first irrigation liquid inlet opening, the second irrigation liquid inlet opening, the first irrigation liquid outlet opening and the second irrigation liquid outlet opening, wherein the first connector is configured to detachably connect in a liquid-tight manner to the first irrigation liquid inlet opening and to the second irrigation liquid inlet opening and the second connector is configured to detachably connect in a liquid-tight manner to the first irrigation liquid outlet opening and to the second irrigation liquid outlet opening and wherein the first irrigation liquid inlet opening and the second irrigation liquid inlet opening are connected with one another in a liquid-conveying manner in the prosthesis body and the first irrigation liquid outlet opening and the second irrigation liquid outlet opening are connected with one another in a liquid-conveying manner in the prosthesis body.

13. The hip joint spacer according to claim 1, wherein the sum of the cross-sectional areas of all of the at least one irrigation liquid intake opening together is at least as great as the cross-sectional area of the irrigation liquid inlet opening, or the sum of the cross-sectional areas of all of the at least one irrigation liquid discharge opening is at least as great as the cross-sectional area of the irrigation liquid outlet opening, or both.

14. The hip joint spacer according to claim 1, wherein the at least one irrigation liquid discharge opening and the at least one irrigation liquid intake opening are arranged outside the sliding surface of the ball head.

15. The hip joint spacer according to claim 1, further comprising at least one of:
   a first valve element arranged in the first connector or in the irrigation liquid inlet opening, the first valve element preventing backflow of the irrigation liquid into the first connector, or
   a second valve element arranged in the second connector or in the irrigation liquid outlet opening, the second valve element preventing backflow of the irrigation liquid into the second connector.

16. The hip joint spacer according to claim 1, further comprising at least one of:
   a first valve arranged in a first duct inside the prosthesis body which connects the at least one irrigation liquid intake opening in a liquid-conveying manner to the irrigation liquid outlet opening, the first valve being openable solely by applying a vacuum at the irrigation liquid outlet opening and preventing backflow of the irrigation liquid into the first duct, or
   a second valve arranged in a second duct inside the prosthesis body which connects the at least one irrigation liquid discharge opening in a liquid-conveying manner to the irrigation liquid inlet opening, the second valve being openable solely by applying a vacuum at the irrigation liquid inlet opening and preventing backflow of the irrigation liquid into the second duct.

17. The hip joint spacer according to claim 1, wherein the irrigation liquid inlet opening, the irrigation liquid outlet opening, the at least one irrigation liquid discharge opening, the at least one irrigation liquid intake opening and the liquid-conveying connectors are formed in the prosthesis body, and the prosthesis body is made of plastic, metal, ceramic, glass ceramic, bone cement or a combination thereof.

18. The hip joint spacer according to claim 1, wherein the irrigation liquid inlet opening and the irrigation liquid outlet opening are arranged in a lateral surface of the neck or in the distal side of the ball head or of the collar.

19. The hip joint spacer according to claim 1, wherein at least one irrigation liquid discharge opening of the at least one irrigation liquid discharge opening is arranged at the end of the stem.

20. The hip joint spacer according to claim 1, further comprising a fastener and a plurality of head parts each having ball heads of different diameters, wherein, the prosthesis body has a multipart configuration including the stem and at least one head part which are configured to be connected via the fastener.

* * * * *